(12) United States Patent
Cumming et al.

(10) Patent No.: US 7,658,938 B2
(45) Date of Patent: Feb. 9, 2010

(54) SOLID ORAL DOSAGE FORM CONTAINING AN ENHANCER

(75) Inventors: Kenneth Iain Cumming, Dublin (IE); Zebunnissa Ramtoola, Dublin (IE)

(73) Assignee: Merrion Reasearch III Limited, Dublin (IE)

( * ) Notice: Subject to any disclaimer, the term of this patent is extended or adjusted under 35 U.S.C. 154(b) by 0 days.

(21) Appl. No.: 09/510,560

(22) Filed: Feb. 22, 2000

(65) Prior Publication Data

US 2003/0091623 A1    May 15, 2003

Related U.S. Application Data

(60) Provisional application No. 60/121,048, filed on Feb. 22, 1999.

(51) Int. Cl.
*A61K 9/00* (2006.01)

(52) U.S. Cl. .................. 424/408; 424/464; 424/469

(58) Field of Classification Search ................ 424/451, 424/463, 464, 474, 452, 489
See application file for complete search history.

(56) References Cited

U.S. PATENT DOCUMENTS

| | | | |
|---|---|---|---|
| 4,525,339 A | 6/1985 | Behl et al. ............... 424/16 |
| 4,656,161 A | 4/1987 | Herr ....................... 514/56 |
| 4,789,547 A | 12/1988 | Song et al. |
| 5,169,933 A | 12/1992 | Anderson et al. |
| 5,190,748 A | 3/1993 | Bachynsky et al. ...... 424/78.08 |
| 5,221,734 A * | 6/1993 | Burk et al. .............. 530/399 |
| 5,229,130 A | 7/1993 | Sharma et al. ........... 424/449 |
| 5,288,497 A | 2/1994 | Stanley et al. |
| 5,346,701 A * | 9/1994 | Heiber et al. ............ 424/435 |
| 5,541,155 A | 7/1996 | Leone-Bay et al. |
| 5,631,347 A | 5/1997 | Baker et al. |
| 5,650,386 A | 7/1997 | Leone-Bay et al. |
| 5,714,477 A * | 2/1998 | Einarsson ................ 514/56 |
| 5,736,161 A * | 4/1998 | Garces et al. ............ 424/493 |
| 5,840,685 A | 11/1998 | Fujii et al. |
| 5,854,281 A | 12/1998 | Uekama et al. |
| 5,863,555 A | 1/1999 | Heiber et al. |

(Continued)

FOREIGN PATENT DOCUMENTS

EP    0370481 A2    11/1989

(Continued)

OTHER PUBLICATIONS

Oda et al., Proc. Int'l Symp. Control. Rel. Bioact. Mater. 24 (1997) pp. 283-284.*

(Continued)

*Primary Examiner*—Jeffrey S. Lundgren
(74) *Attorney, Agent, or Firm*—Myers Bigel Sibley & Sajovec, P.A.

(57) ABSTRACT

The invention relates to a solid oral dosage form comprising a pharmaceutically active ingredient in combination with an enhancer which enhances the bioavailability and/or the absorption of the active ingredient. Accordingly, a solid oral dosage form comprises a drug and an enhancer wherein the enhancer is a medium chain fatty acid ester, ether or salt or a derivative of a medium chain fatty acid, which is, preferably, solid at room temperature and which has a carbon chain length of from 6 to 20 carbon atoms. Preferably, the solid oral dosage form is controlled release dosage form such as a delayed release dosage form.

53 Claims, 15 Drawing Sheets

U.S. PATENT DOCUMENTS

| | | | |
|---|---|---|---|
| 5,912,009 | A | 6/1999 | Venkateshwaran et al. |
| 5,952,000 | A | 9/1999 | Venkateshwaran et al. |
| 5,977,175 | A * | 11/1999 | Lin .............................. 514/558 |
| 6,001,390 | A | 12/1999 | Yum et al. |
| 6,017,559 | A | 1/2000 | Mulqueen et al. |
| 6,124,261 | A | 9/2000 | Stevenson et al. |
| 6,200,602 | B1 | 3/2001 | Watts et al. |
| 6,270,804 | B1 | 8/2001 | Getz et al. |
| 6,326,360 | B1 | 12/2001 | Kanazawa et al. |
| 6,372,728 | B1 | 4/2002 | Ungell |
| 6,379,960 | B1 | 4/2002 | Popoff et al. |
| 6,468,559 | B1 | 10/2002 | Chen et al. |
| 6,638,530 | B1 | 10/2003 | Ishibashi et al. |
| 6,747,014 | B2 * | 6/2004 | Teng et al. .................... 514/44 |
| 7,154,002 | B1 | 12/2006 | Bressi et al. |
| 2003/0176397 | A1 | 9/2003 | Lichtenberger |
| 2004/0087631 | A1 | 5/2004 | Bacopoulos et al. |
| 2006/0210639 | A1 | 9/2006 | Liversidge et al. |
| 2007/0060509 | A1 | 3/2007 | Kanikanti et al. |
| 2007/0148228 | A1 | 6/2007 | Cumming et al. |
| 2007/0196464 | A1 | 8/2007 | Cumming et al. |
| 2007/0238707 | A1 | 10/2007 | Leonard |
| 2007/0292512 | A1 | 12/2007 | Leonard et al. |
| 2008/0275001 | A1 | 11/2008 | Cumming et al. |

FOREIGN PATENT DOCUMENTS

| | | |
|---|---|---|
| EP | 0376534 A1 | 7/1990 |
| EP | 0497162 | 8/1992 |
| EP | 0517211 | 12/1992 |
| EP | 0580074 A1 | 1/1994 |
| GB | 953626 | 3/1964 |
| IE | (11) 63119 | 11/1989 |
| IE | (11)63119 * | 3/1995 |
| JP | 59 073600 | 4/1984 |
| JP | 03 275633 | 12/1991 |
| RU | 2068689 | 11/1996 |
| WO | WO 8404674 A1 * | 12/1984 |
| WO | WO 93/05903 A1 | 4/1993 |
| WO | WO 93/21907 | 11/1993 |
| WO | WO 9522319 A1 * | 8/1995 |
| WO | WO 9534294 | 12/1995 |
| WO | WO 97/05903 * | 2/1997 |
| WO | WO 99/01579 | 1/1999 |
| WO | WO 99/02120 A2 | 1/1999 |
| WO | WO 99/02485 A1 | 1/1999 |
| WO | WO 99/45934 A1 | 9/1999 |
| WO | WO 00/22909 A2 | 4/2000 |
| WO | WO 00/50012 | 8/2000 |
| WO | WO 02/092070 | 11/2002 |
| WO | WO 03/047493 A2 | 6/2003 |
| WO | WO 2005/055973 A2 | 6/2005 |

OTHER PUBLICATIONS

Appendix A: Webpage publication provided by Lambent Technologies—www.petroferm.com/prodinfo.asp?bus=2&mkt=4&app=3.*
Lambent Technologies: Technical Data Sheet for Lumulse L-4, Lumulse L-12 and Lumulse L-23.*
"McGraw-Hill Dictionary of Chemical Terms"; McGraw-Hill Book Company: Ed. S.P. Parker, New York 1985 (pp. 208, 209 and 251).*
Andriuoli et al.,. Haemostasis 20(suppl 1):154-158 (1990).*
Lindmark et al., J. Pharm. Ex. Therapeutics275(2):958-964 (1995).*
Aungst, B.J. et al., Enhancement of the Intestinal Absorption of Peptides and Non-peptides, J. of Controlled Release (1996), 41:19-31.
Lindmark, T. et al., Mechanism of Absorption Enhancement in Humans After Rectal Administration of Ampicillin in Suppositories Containing Sodium Caprate, Pharmaceutical Research (1997), 14: 930-935.
Anderberg, E.K. et al., Sodium Caprate Elicits Dilatations in Human Intestinal Tight Junctions and Enhances Drug Absorption by the Paracellular Route, Pharmaceutical Research (1993), 10: 857-864.
Yeh, P. et al., Effect of Medium-chain Glycerides on Physiological Properties of Rabbit Intestinal Epithelium in Vitro, Pharmaceutical Resarch-(1994), 11:1148-1154.
Artursson, P., Epithelial Transport of Drugs in Cell Culture. I: A Model for Studying the Passive Diffusion of Drugs over Intestinal Absorbative (Caco-2) Cells, J. Pharmaceutical Studies (1990), 79: 476-482.
Doluisio, J.T. et al., Drug Absorption I: An In Situ Rat Gut Technique Yielding Realistic Absorption Rates, J. Pharmaceutical Studies (1969), 59: 1196-1200.
Brayden, D. et al., Heparin Absorption Across the Intestine: Effects of Sodium N-[8-(2-Hydroxybenzoyl)Amino]Caprylate In Rat In Situ Intestinal Instillations and in Caco-2 Monolayers, Pharmaceutical Research (1997), 14:1772-1779.
Cumming, K.I. and A.J. Winfield, In Vitro Evaluation of a Series of Sodium Carboxylates as Dermal Penetration Enhancers, Int. J. Pharm. (1994), 108: 141-148.
Tomita, M. et al., Enhancement of Colonic Drug Absorption by the Paracellular Permeation Route, Pharmaceutical Research (1988), 5: 341-346.
Aungst, Bruce K. et al., Enhancement of the Intestinal Absorption of Peptides and Non-Peptides, Journal of Controlled Release 41 (1996) pp. 19-31.
Palin, K. J. et al., The Oral Absorption of Cefoxitin from Oil and Emulsion Vehicles in Rats, International Journal of Pharmaceutics, 33 (1986) pp. 99-104.
Tomita, M. et al., Enhancement of Colonic Drug Absorption by the Paracellular Permeation Route, Pharmaceutical Research vol. 5, No. 6, (1988), pp. 341-346.
Murakami, M. et al., Effect of Oleic Acid Vesicles on Intestinal Absorption of Carboxyfluorescein in Rats, Pharmaceutical Research, vol. 3, No. 1, 1986, pp. 35-40.
Muranushi, N. et al., The Effects Of Fatty Acids and Their Derivatives on The Intestinal Absorption of Insulin In Rats, Drug Development and Industrial Pharmacy, 19(8), pp. 929-941 (1993).
Tomita, M. et al., Differences in the Enhancing Effects of Sodium Caprate on Colonic and Jejunal Drug Absorption, Pharmaceutical Research, vol. 9, No. 5, 1992, pp. 648-653.
Tomita, M. et al., Enhancement of Colonic Drug Absorption by the Transcellular Permeation Route, Pharmaceutical Research vol. 5., No. 12 (1988), pp. 786-789.
Anderberg, E. K. et al., Sodium Caprate Elicits Dilatations in Human Intestinal Tight Junctions and Enhances Drug Absorption by the Paracellular Route, Pharmaceutical Research vol. 10, No. 6, 1993, pp. 857-864.
Tomita, Mikio, et al., Absorption-Enhancing Mechanism of Sodium Caprate and Decanoylcarnitine in Caco-2 Cells, The Journal of Pharmacology and Experimental Therapeutics, vol. 272, No. 2, 1995, pp. 739-743.
Sawada, T., et al., Role of Paracellular Pathway in Nonelectrolyte Permeation Across Rat Colon Epithelium Enhanced by Sodium Caprate and Sodium Caprylate, Pharmaceutical Research, vol. 8, No. 11, 1991, pp. 1365-1371.
Aungst, "Structure/effect studies of fatty acid isomers as skin penetration enhancers and skin irritants," Pharm. Res. 6:244-247 (1989).
Chan et al., "Depsipeptide (FR901228, NSC-630176) pharmacokinetics in the rat by LC/MS/MS," Invest. New Drugs 15:195-206 (1997).
Mishima et al., "Studies on the Promoting Effects of Medium Chain Fatty Acid Salts on the Nasal Absorption of Insulin in Rats," J. Pharmacobio-Dyn., 10:624-631 (1987).
Morishita et al., "Site-Dependent Effect of Aprotinin, Sodium Caprate, Na₂EDTA and Sodium Glycocholate on Intestinal Absorption of Insulin," Biol. Pharm. Bull. 16:68-72 (1993).
Schneider et al., "Evaluation of drug penetration into human skin ex vivo using branched fatty acids and propylene glycol," Int. J. Pharm. 145:187-196 (1996).
Yamamoto et al., "Pulmonary absorption enhancement of peptides by absorption enhancers and protease inhibitors," J. Control. Release, 41:57-67 (1996).

Yang et al., Deposition of insulin powders for inhalation in vitro and pharmacodynamic evaluation of absorption promoters in rats, Acta Pharmaceutica Sinica 40:1069-1074 (2005).

Zhou et al., "Effects of cholic acid and other enhancers on the bioavailability of insulin from a subcutaneous site," Int. J. Pharm. 69:29-41 (1991).

U.S. Appl. No. 11/450,641, filed Jun. 9, 2006; Office Action Mailed Jun. 25, 2009.

U.S. Appl. No. 11/733,007, filed Apr. 9, 2007; Office Action Mailed Aug. 17, 2009.

Lambent Technologies, "Material Safety Data Sheet for Lumulse L-12", pp. 1-3 (2004).

WPI Database, Accession No. 1984-142694, English language abstract of JP 59073600.

WPI Database, Accession No. 1992-028863, English language abstract of JP 03275633.

WPI Database, Accession No. 1997-287727, English language abstract of RU 2068689.

U.S. Appl. No. 11/761,233, filed Jun. 11, 2007; Office Action mailed Sep. 1, 2009.

U.S. Appl. No. 12/481,952, filed Jun. 10, 2009.

U.S. Appl. No. 12/553,196, filed Sep. 3, 2009.

U.S. Appl. No. 11/400,689, filed Apr. 7, 2006; Office Action Mailed Feb. 12, 2009.

U.S. Appl. No. 11/733,007, filed Apr. 9, 2007; Office Action Mailed Jan. 29, 2009.

Bennett et al., "Pulmonary Delivery of Detirelex by Intratracheal Instillation and Aerosol Inhalation in the Briefly Anesthetized Dog," Pharm. Res. 11:1048-1054 (1994).

Declaration of Dr. Thomas W. Leonard from European Patent Application EP 00905186.3.

Gennaro, "Remington: The Science and Practice of Pharmacy," $19^{th}$ Edition, Mack Publishing Co., p. 1618 (1995).

Lambent Technologies, "Technical Data Sheet for Lumulse L-4, Lumulse L-12, and Lumulse L-23", pp. 1-2 (2004).

Muranishi, "Absorption Enhancers," Crit. Rev. Ther. Drug Carrier Systems 7:1-33 (1990).

* cited by examiner

SOLID ORAL DOSAGE FORM CONTAINING AN ENHANCER

This application claims priority of U.S. Provisional Application No. 60/121,048 which was filed on Feb. 22, 1999.

FIELD OF THE INVENTION

The present invention relates to a solid oral dosage form containing enhancers. In particular the invention relates to a solid oral dosage form comprising a pharmaceutically active ingredient in combination with an enhancer which enhances the bioavailability and/or the absorption of the active ingredient and which is a controlled release dosage form such as a delayed release dosage form.

BACKGROUND OF THE INVENTION

The epithelial cells lining the lumenal side of the GIT are a major barrier to drug delivery following oral administration. However, there are four recognised transport pathways which can be exploited to facilitate drug delivery and transport: the transcellular, paracellular, carrier-mediated and transcytotic transport pathways. The ability of a drug, such as a conventional drug, a peptide, a protein, a macromolecule or a nano- or microparticulate system, to "interact" with one or more of these transport pathways may result in increased delivery of that drug from the GIT to the underlying circulation.

Certain drugs utilise transport systems for nutrients which are located in the apical cell membranes (carrier mediated route). Macromolecules may also be transported across the cells in endocytosed vesicles (transcytosis route). However, many drugs are transported across the intestinal epithelium by passive diffusion either through cells (transcellular route) or between cells (paracellular). Most orally administered drugs are absorbed by passive transport. Drugs which are lipophilic permeate the epithelium by the transcellular route whereas drugs that are hydrophilic are restricted to the paracellular route.

Paracellular pathways occupy less than 0.1% of the total surface area of the intestinal epithelium. Further, tight junctions, which form a continuous belt around the apical part of the cells, restrict permeation between the cells by creating a seal between adjacent cells. Thus, oral absorption of hydrophilic drugs such as peptides can be severely restricted. Other barriers to absorption of drugs may include hydrolysing enzymes in the lumen brush border or in the intestinal epithelial cells, the existence of the aqueous boundary layer on the surface of the epithelial membrane which may provide an additional diffusion barrier, the mucus layer associated with the aqueous boundary layer and the acid microclimate which creates a proton gradient across the apical membrane. Absorption, and ultimately bioavailability, of a drug may also be reduced by other processes such as P-glycoprotein regulated transport of the drug back into the gut lumen and cytochrome P450 metabolism.

Therefore, new strategies for delivering drugs across the GIT cell layers are needed, particularly for hydrophilic drugs including peptides, proteins and macromolecular drugs.

Numerous potential absorption enhancers have been identified. For instance, medium chain glycerides have demonstrated the ability to enhance the absorption of hydrophilic drugs across the intestinal mucosa (*Pharm. Res.* (1994), 11, 1148-54). However, the importance of chain length and/or composition is unclear and therefore their mechanism of action remains largely unknown. Sodium caprate has been reported to enhance intestinal and colonic drug absorption by the paracellular route (*Pharm. Res.* (1993) 10, 857-864; *Pharm. Res.* (1988), 5, 341-346). U.S. Pat. No. 4,656,161 (BASF AG) discloses a process for increasing the enteral absorbability of heparin and heparinoids by adding non-ionic surfactants such as those that can be prepared by reacting ethylene oxide with a fatty acid, a fatty alcohol, an alkylphenol or a sorbitan or glycerol fatty acid ester. U.S. Pat. No. 5,229,130 (Cygnus Therapeutics Systems) discloses a composition which increases the permeability of skin to a transdermally administered pharmacologically active agent formulated with one or more vegetable oils as skin permeation enhancers. Dermal penetration is also known to be enhanced by a range of sodium carboxylates [*Int. J. of Pharmaceutics* (1994), 108, 141-148]. Additionally, the use of essential oils to enhance bioavailability is known (U.S. Pat. No. 5,66,386 AvMax Inc. and others). It is taught that the essential oils act to reduce either, or both, cytochrome P450 metabolism and P-glycoprotein regulated transport of the drug out of the blood stream back into the gut.

Often, however, the enhancement of drug absorption correlates with damage to the intestinal wall. Consequently, limitations to the widespread use of GIT enhancers is frequently determined by their potential toxicities and side effects. Additionally and especially with respect to peptide, protein or macromolecular drugs, the "interaction" of the GIT enhancer with one of the transport pathways should be transient or reversible, such as a transient interaction with or opening of tight junctions so as to enhance transport via the paracellular route.

As mentioned above, numerous potential enhancers are known. However, this has not led to a corresponding number of products incorporating enhancers. One such product currently approved for use in Sweden and Japan is the Doktacillin™ suppository [Lindmark et al. *Pharmaceutical Research* (1997), 14, 930-935]. The suppository comprises ampicillin and the medium chain fatty acid, sodium caprate (C10).

Provision of a solid oral dosage form which would facilitate the administration of a drug together with an enhancer is desirable. The advantages of solid oral dosage forms over other dosage forms include ease of manufacture, the ability to formulate different controlled release and extended release formulations and ease of administration. Administration of drugs in solution form does not readily facilitate control of the profile of drug concentration in the bloodstream. Solid oral dosage forms, on the other hand, are versatile and may be modified, for example, to maximise the extent and duration of drug release and to release a drug according to a therapeutically desirable release profile. There may also be advantages relating to convenience of administration increasing patient compliance and to cost of manufacture associated with solid oral dosage forms.

SUMMARY OF THE INVENTION

According to the present invention, a solid oral dosage form comprises a drug and an enhancer wherein the enhancer is a medium chain fatty acid salt, ester, ether or a derivative of a medium chain fatty acid which is, preferably, solid at room temperature and which has a carbon chain length of from 6 to 20 carbon atoms; with the provisos that (i) where the enhancer is an ester of a medium chain fatty acid, said chain length of from 6 to 20 carbon atoms relates to the chain length of the carboxylate moiety, and (ii) where the enhancer is an ether of a medium chain fatty acid, at least one alkoxy group has a carbon chain length of from 6 to 20 carbon atoms.

Preferably, the enhancer is a medium chain fatty acid salt, ester, ether or a derivative of a medium chain fatty acid which is, preferably, solid at room temperature and which has a carbon chain length of from 8 to 14 carbon atoms; with the provisos that (i) where the enhancer is an ester of a medium chain fatty acid, said chain length of from 8 to 14 carbon atoms relates to the chain length of the carboxylate moiety, and (ii) where the enhancer is an ether of a medium chain fatty acid, at least one alkoxy group has a carbon chain length of from 8 to 14 carbon atoms. More preferably, the enhancer is a sodium salt of a medium chain fatty acid, the medium chain fatty acid having a carbon chain length of from 8 to 14 carbon atoms; the sodium salt being solid at room temperature. Most preferably, the enhancer is sodium caprylate, sodium caprate or sodium laurate. The drug and enhancer can be present in a ratio of from 1:100000 to 10:1 (drug:enhancer) preferably, from 1:1000 to 10:1.

In a preferred embodiment of the invention the drug is a macromolecule such as a peptide, protein, oligosaccharide or polysaccharide including TRH, unfractionated heparin, low molecular weight heparin, insulin, luteinising hormone-releasing hormone (LHRH), leuprolide acetate, goserelin, naferelin, buserelin, cyclosporin, calcitonin, vasopressin, desmopressin, an antisense oligonucleotide, alendronate, etidronate or salts thereof.

The solid oral dosage form can be a tablet, a mutiparticulate or a capsule. The multiparticulate can be in the form of a tablet or contained in a capsule. The tablet can be a single or multilayer tablet having compressed multiparticulate in one, all or none of the layers. It is preferably a controlled release dosage form. More preferably, it is a delayed release dosage form. The dosage form can be coated with a polymer, preferably a rate-controlling or a delayed release polymer. The polymer can also be compressed with the enhancer and drug to form a matrix dosage form such as a controlled release matrix dosage form. A polymer coating can then be applied to the matrix dosage form.

Other embodiments of the invention include the process of making the solid oral dosage forms, methods of treating a condition by administering the solid oral dosage forms to a patient and use of a drug and enhancer in the manufacture of a medicament.

DETAILED DESCRIPTION OF THE INVENTION

Figure 1:
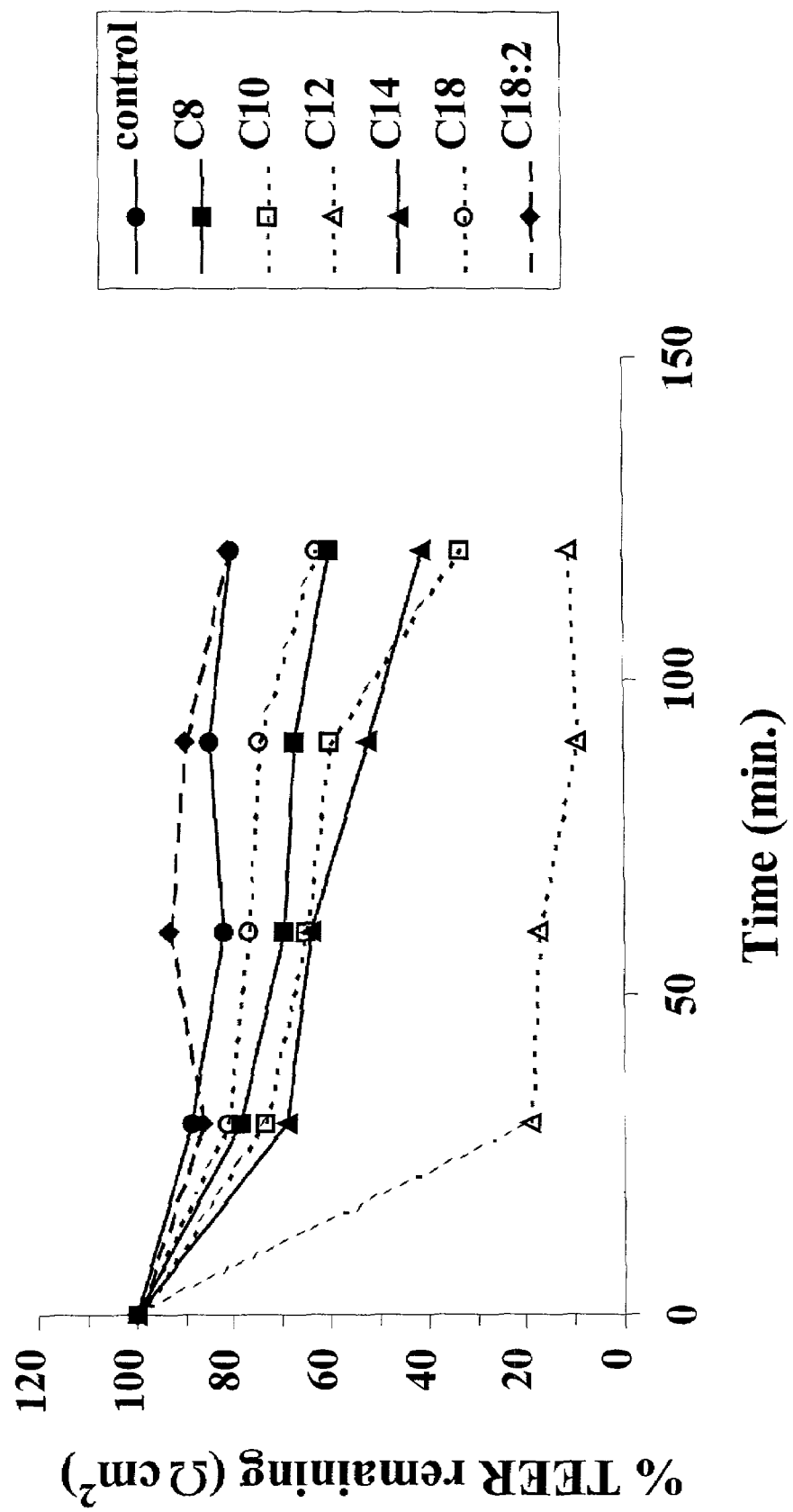
FIG. 1 shows the effect of the sodium salts of C8, C10, C12, C14, C18 and C18:2 with $^3$H-TRH on TEER ($\Omega$cm$^2$) in Caco-2 monolayers at time 0 and at 30 min. intervals up to 2 hours as described in Example 1.

As used in this specification and appended claims, the singular forms "a", "an" and "the" include plural referents unless the content clearly dictates otherwise. Thus, for example, reference to "an enhancer" includes a mixture of one or more enhancers, reference to "a drug" includes reference to one or more drugs, and the like.

As used herein, the term "enhancer" refers to a compound (or mixture of compounds) which is capable of enhancing the transport of a drug, particularly a hydrophilic and/or macromolecular drug across the GIT in an animal such as a human, wherein the enhancer is a medium chain fatty acid salt, ester or ether or a derivative of a medium chain fatty acid that is, preferably, solid at room temperature and that has a carbon chain length of from 6 to 20 carbon atoms; with the provisos that (i) where the enhancer is an ester of a medium chain fatty acid, said chain length of from 6 to 20 carbon atoms relates to the chain length of the carboxylate moiety, and (ii) where the enhancer is an ether of a medium chain fatty acid, at least one alkoxy group has a carbon chain length of from 6 to 20 carbon atoms. Preferably, the enhancer is a sodium salt of a medium chain fatty acid. Most preferably, the enhancer is sodium caprate.

As used herein, a "derivative of a medium chain fatty acid" comprises a fatty acid derivative having at least one carbon chain of from 6 to 20 carbon atoms in length. This carbon chain may be characterised by various degrees of saturation. In other words, the carbon chain may be, for example, fully saturated or partially unsaturated (i.e. containing one or more carbon-carbon multiple bonds). The term "fatty acid derivative" is meant to encompass acyl derivatives such as esters, acid halides, anhydrides, amides and nitrites, and also ethers and glycerides such as mono-, di- or tri-glycerides. The term "fatty acid derivative" is meant to further encompass medium chain fatty acids wherein the end of the carbon chain opposite the acid group (or derivative) is also functionalised with one of the above mentioned moieties (i.e. ester, acid halide, anhydride, amide, nitrile, ether and glyceride moieties). Such difunctional fatty acid derivatives thus include for example diacids and diesters (the functional moieties being of the same kind) and also difunctional compounds comprising different functional moieties, such as amino acids and amino acid derivatives (for example a medium chain fatty acid, or an ester or a salt thereof, comprising an amide moiety at the opposite end of the fatty acid carbon chain to the acid (or ester or salt thereof).

As used herein, the term "drug" includes any drug, including conventional drugs, appropriate for administration via the oral route to an animal including a human. The term "drug" also explicitly includes those entities that are poorly absorbed via the oral route including hydrophilic drugs or macromolecular drugs such as peptides, proteins, oligosaccharides, polysaccharides or hormones including, but not limited to, insulin, calcitonin, calcitonin gene regulating protein, atrial natriuretic protein, colony stimulating factor, betaseron, erythropoietin (EPO), interferons, somatropin, somatotropin, somatostatin, insulin-like growth factor (somatomedins), luteinizing hormone releasing hormone (LHRH), tissue plasminogen activator (TPA), thyrotropin releasing hormone (TRH), growth hormone releasing hormone (GHRH), antidiuretic hormone (ADH) or vasopressin and analogues thereof such as for example desmopressin, parathyroid hormone (PTH), oxytocin, estradiol, growth hormones, leuprolide acetate, goserelin acetate, naferelin, buserelin, factor VIII, interleukins such as interleukin-2, and analogues thereof and anti-coagulant agents such as heparin, heparinoids, low molecular weight heparin, hirudin, and analogues thereof, bisphosphonates including alendronate and etidronate, pentassacharides including anticoagulent pentassacharides, antigens, adjuvants and the like. The drug compound itself may be in the form of nano-, micro- or larger particles in crystalline or amorphous form.

The drug can be included in a nano- or microparticulate drug delivery systems in which the drug is entrapped, encapsulated by, associated with, or attached to a nano- or microparticle. Preferably, the drug is in a crystalline or amorphous form or in a form that does not include being associated with a nano- or microparticle.

As used herein, a "therapeutically effective amount of a drug" refers to an amount of drug that elicits a therapeutically useful response in an animal, preferably a mammal, most preferably a human.

As used herein, a "therapeutically effective amount of an enhancer" refers to an amount of enhancer that allows for uptake of therapeutically effective amounts of the drug via oral administration. It has been shown that the effectiveness of an enhancer in enhancing the gastrointestinal delivery of poorly permeable drugs is dependent on the site of administration (see Examples 6, 7 and 12), the site of optimum delivery being dependent on the drug and enhancer.

A solid oral dosage form according to the present invention may be a tablet, a multiparticulate or a capsule. A preferred solid oral dosage form is a delayed release dosage form which minimises the release of drug and enhancer in the stomach, and hence the dilution of the local enhancer concentration therein, and releases the drug and enhancer in the intestine. A particularly preferred solid oral dosage form is a delayed release rapid onset dosage form. Such a dosage form minimises the release of drug and enhancer in the stomach, and hence the dilution of the local enhancer concentration therein, but releases the drug and enhancer rapidly once the appropriate site in the intestine has been reached, maximising the delivery of the poorly permeable drug by maximising the local concentration of drug and enhancer at the site of absorption The term "tablet" as used herein includes, but is not limited to, immediate release (IR) tablets, sustained release (SR) tablets, matrix tablets, multilayer tablets, multilayer matrix tablets, extended release tablets, delayed release tablets and pulsed release tablets any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms particularly useful in the practice of the invention include those selected from the group consisting of IR tablets, SR tablets, coated IR tablets, matrix tablets, coated matrix tablets, multilayer tablets, coated multilayer tablets, multilayer matrix tablets and coated multilayer matrix tablets. A preferred tablet dosage form is an enteric coated tablet dosage form. A particularly preferred tablet dosage form is an enteric coated rapid onset tablet dosage form.

Capsule solid oral dosage forms particularly useful in the practice of the current invention include those selected from the group consisting of instant release capsules, sustained release capsules, coated instant release capsules, coated sustained release capsules including delayed release capsules. A preferred capsule dosage form is an enteric coated capsule dosage form. A particularly preferred capsule dosage form is an enteric coated rapid onset capsule dosage form.

The term "multiparticulate" as used herein means a plurality of discrete particles, pellets, mini-tablets and mixtures or combinations thereof. If the oral form is a multiparticulate capsule, such hard or soft gelatin capsules can suitably be used to contain the multiparticulate. Alternatively a sachet can suitably be used to contain the multiparticulate. If desired, the multiparticulate may be coated with a layer containing rate controlling polymer material. A multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

Alternatively, the multiparticulate and one or more auxiliary excipient materials can be compressed into tablet form such as a multilayer tablet. Typically, a multilayer tablet may comprise two layers containing the same or different levels of the same active ingredient having the same or different release characteristics. Alternatively, a multilayer tablet may contain different active ingredient in each layer. Such a tablet, either single layered or multilayered, can optionally be coated with a controlled release polymer so as to provide additional controlled release properties. A preferred multiparticulate dosage form comprises a capsule containing delayed release rapid onset minitiablets. A particularly preferred multiparticulate dosage form comprises a delayed release capsule comprising instant release minitablets. A most preferred multiparticulate dosage form comprises a capsule comprising delayed release granules. A most particularly preferred multiparticulate dosage form comprises a delayed release capsule comprising instant release granules.

A number of preferred embodiments of the invention will now be described. In each case the drug may be present in any amount which is sufficient to elicit a therapeutic effect and, where applicable, may be present either substantially in the form of one optically pure enantiomer or as a mixture, racemic or otherwise, of enantiomers. The drug compound is suitably present in any amount sufficient to elicit a therapeutic effect. As will be appreciated by those skilled in the art, the actual amount of drug compound used will depend on the potency of the drug compound in question. The amount of drug compound may suitably be in the range of from about 0.5 µg to about 1000 mg. The enhancer is suitably present in any amount sufficient to allow for uptake of therapeutically effective amounts of the drug via oral administration. Preferably the drug and the enhancer are present in a ratio of from 1:100000 to 10:1 (drug:enhancer), preferably the ratio is from 1:1000 to 10:1. The actual ratio of drug to enhancer used will depend on the potency of the drug compound and the enhancing activity of the enhancer.

In a first embodiment, a solid oral dosage form according to the invention comprises a drug and an enhancer in admixture compressed into a tablet.

In a second embodiment, a solid oral dosage form according to the invention comprises a drug, an enhancer and a rate controlling polymer material in admixture compressed into a tablet. The term "rate controlling polymer material" as used herein includes hydrophilic polymers, hydrophobic polymers and mixtures of hydrophilic and/or hydrophobic polymers that are capable of controlling or retarding the release of the drug compound from a solid oral dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose, hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly (alkylmethacrylate) and poly (vinyl acetate). Other suitable hydrophobic polymers include polymers and/or copolymers derived from acrylic or methacrylic acid and their respective esters, zein, waxes, shellac and hydrogenated vegetable oils. Particularly useful in the practice of the present invention are poly acrylic acid, poly acrylate, poly methacrylic acid and poly methacrylate polymers such as those sold under the Eudragit tradename (Rohm GmbH, Darmstadt, Germany) specifically Eudragit® L, Eudragit® S, Eudragit® RL, Eudragit® RS coating materials and mixtures thereof. Some of these polymers can be used as delayed release polymers to control the site where the drug is released. They include poly methacrylate polymers such as those sold under the Eudragit tradename (Rohm GmbH, Darmstadt, Germany) specifically Eudragit® L, Eudragit® S, Eudragit® RL, Eudragit® RS coating materials and mixtures thereof.

In a third embodiment, a solid oral dosage form according to the invention comprises a multilayer table. Typically such a multilayer tablet may comprise a first layer containing a drug and an enhancer in an instant release form and a second layer containing a drug and an enhancer in a sustained, extended, controlled or modified release form. In an alternative embodiment, a multilayer tablet may comprise a first layer containing a drug and a second layer containing an enhancer. Each layer may independently comprise further excipients chosen to modify the release of the drug or the enhancer. Thus the drug and the enhancer may be released from the respective first and second layers at rates which are the same or different. Alternatively, each layer of the multilayer tablet may comprise both drug and enhancer in the same or different amounts.

A fourth embodiment a solid oral dosage form according to the invention comprises a drug and an enhancer in admixture in the form of a multiparticulate. The drug and enhancer may be contained in the same or different populations of particles, pellets or mini-tablets making up the multiparticulate. If the solid oral dosage form is a multiparticulate, sachets and capsules such as hard or soft gelatin capsules can suitably be used to contain the multiparticulate. A multiparticulate solid oral dosage form according to the invention may comprise a blend of two or more populations of particles, pellets or mini-tablets having different in vitro and/or in vivo release characteristics. For example, a multiparticulate oral dosage form may comprise a blend of an immediate release component and a delayed release component contained in a suitable capsule.

In the case of any of the above-mentioned embodiments, a controlled release coating may be applied to the final dosage form (capsule, tablet, multilayer tablet etc.). The controlled release coating may typically comprise a rate controlling polymer material as defined above. The dissolution characteristics of such a coating material may be pH dependent or independent of pH.

The various embodiments of the solid oral dosage forms of the invention may further comprise auxiliary excipients such as for example diluents, lubricants, disintegrants, plasticisers, anti-tack agents, opacifying agents, pigments, flavourings and such like. As will be appreciated by those skilled in the art, the exact choice of excipients and their relative amounts will depend to some extent on the final dosage form.

Suitable diluents include for example pharmaceutically acceptable inert fillers such as microcrystalline cellulose, lactose, dibasic calcium phosphate, saccharides, and/or mixtures of any of the foregoing. Examples of diluents include microcrystalline cellulose such as that sold under the Trademark Avicel (FMC Corp., Philedelphia, Pa.) for example Avicel™ pH101, Avicel™ pH102 and Avicel™ pH112; lactose such as lactose monohydrate, lactose anhydrous and Pharmatose DCL21; dibasic calcium phosphate such as Emcompress; mannitol; starch; sorbitol; sucrose; and glucose.

Suitable lubricants, including agents that act on the flowability of the powder to be compressed are, for example, colloidal silicon dioxide such as Aerosil™ 200; talc; stearic acid, magnesium stearate, and calcium stearate.

Suitable disintegrants include for example lightly crosslinked polyvinyl pyrrolidone, corn starch, potato starch, maize starch and modified starches, croscarmellose sodium, cross-povidone, sodium starch glycolate and combinations and mixtures thereof.

EXAMPLE 1

TRH Containing Tablets (a) Caco-2 monolayers.

Cell Culture: Caco-2 cells were cultured in Dulbecco's Modified Eagles Medium (DMEM) 4.5 g/L glucose supplemented with 1% (v/v) non-essential amino acids; 10% foetal calf serum and 1% penicillin/streptomycin. The cells were cultured at 37° C. and 5% $CO_2$ in 95% humidity. The cells were grown and expanded in standard tissue culture flasks and were passaged once they attained 100% confluence. The Caco-2 cells were then seeded on polycarbonate filter inserts (Costar; 12 mm diameter, 0.4 µm pore size) at a density of $5 \times 10^5$ cells/cm$^2$ and incubated in six well culture plates with a medium change every second day. Confluent monolayers between day 20 and day 30 seeding on filters and at passages 30-40 were used throughout these studies.

Transepithelial Transport Studies: The effects sodium salts of various MCFAs on the transport of $^3$H-TRH (apical to basolateral flux) was examined as follows: 15.0 µCi/ml (0.2 µM) $^3$H-TRH was added apically at time zero for TRH flux experiments. The transport experiments were performed in Hanks Balanced salt solution (HBSS) containing 25 mM N-[2-hydroxyethyl]-piperazine-N'-[2-ethanesulfonic acid] (HEPES) buffer, pH 7.4 at 37° C. Due to variations in solubilities, various concentrations of the different MCFA sodium salts and various apical buffers were used as shown in Table 1. In all cases the basolateral chamber contained regular HBSS+ HEPES.

TABLE 1

Concentrations and buffers used for various MCFA sodium salts

| MCFA salt* | Conc. (mM) | Buffer |
|---|---|---|
| NaC8:0 | 0.32 | HBSS + HEPES |
| NaC10:0 | 0.40 | Ca$^{2+}$ free HBSS |
| NaC12:0 | 3.77 | PBS** |
| NaC14:0 | 1.44 | PBS |
| NaC18:0 | 0.16 | HBSS + HEPES |
| NaC18:2 | 0.16 | HBSS + HEPES |

*In the nomenclature CX:Y for a MCFA salt, X indicates the length of the carbon chain and Y indicates the position of unsaturation, if any.
**PBS—phosphate buffer solution.

After removing the cell culture medium, the monolayers were placed in wells containing prewarmed HBSS (37° C.); 1 ml apically and 2 ml basolaterally. Monolayers were incubated at 37° C. for 30 mins. Then at time zero, apical HBSS was replaced with the relevant apical test solution containing the radiolabelled compounds with and without the enhancer compound. Transepithelial electrical resistance (TEER) of the monolayer was measured at time zero and at 30 min intervals up to 120 min using a Millicell ERS chopstix apparatus (Millipore (U.K.) Ltd., Hertfordshire, UK) with Evom to monitor the integrity of the monolayer. The plates were placed on an orbital shaker in an incubator (37° C.). Transport across the monolayers was followed by basolateral sampling (1 ml) at 30 min. intervals up to 120 mins. At each 30 min. interval each insert was transferred to a new well containing 2 ml fresh prewarmed HBSS. Apical stock radioactivity was determined by taking 10 µl samples at t=0 and t=120 mins. Scintillation fluid (10 ml) was added to each sample and the disintegrations per min. of each sample were determined in a Wallac System 1409 scintillation counter. Mean values for $^3$H-TRH concentrations were calculated for the apical and basolateral solutions at each time point. The apparent permeability coefficients were calculated using the method described by Artursson [Artursson P., *J. Pharm. Sci.* 79:476-482 (1990).

FIG. 1 shows the effect of C8, C10, C12, C14, C18 and C18:2 sodium salts with $^3$H-TRH on TEER ($\Omega$cm$^2$) in Caco-2 monolayers over 2 hours. The data for the C8, C10, C14 and C18 indicate minimal reduction in TEER compared to the control. While the data for C12 indicates some cell damage (reduction in TEER), this reduction is probably a result of the higher concentration of enhancer used in this.

Figure 2:
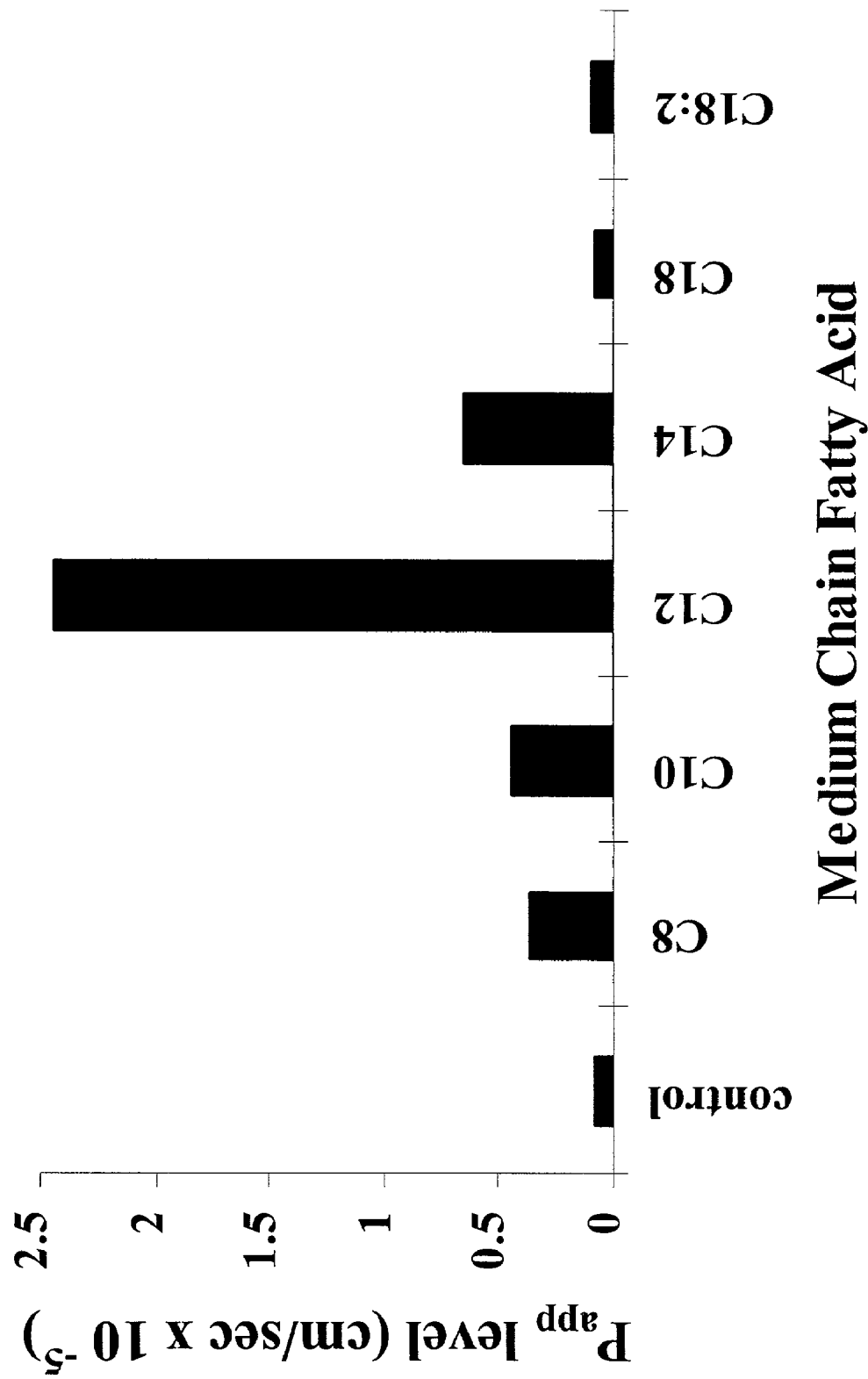
FIG. 2 shows the effect of the sodium salts of C8, C10, C12, C14, C18 and C18:2 on $P_{app}$ for $^3$H-TRH transport in Caco-2 monolayers as described in Example 1.

FIG. 2 shows the effect of C8, C10, C12, C14, C18 and C18:2 sodium salts on $P_{app}$ for $^3$H-TRH across in Caco-2 monolayers. Compared to the control, the sodium salts of C8, C10, C12 and C14 showed considerable increases in the permeability constant, $P_{app}$, at the concentrations used. It is noted that the high $P_{app}$ value observed for the C12 salt may be indicative of cell damage at this high enhancer concentration.

Mitochondrial Toxicity Assay: Mitochondrial dehydrogenase (MDH) activity was assessed as a marker of cell viability using a method based on the colour change of tetrazolium salt in the presence MDH. Cells were harvested, counted and seeded on 96 well plates at an approximate density of 10$^6$ cells/ml (100 µl of cell suspension per well). The cells were then incubated at 37° C. for 24 hours in humidified atmosphere, 5% $CO_2$. A number of wells were treated with each MCFA sodium salt solution at the concentrations shown in Table 1 and the plate was incubated for 2 hours. After incubation 10 µl of MTT labelling reagent was added to each well for 4 hours. Solubilisation buffer (100 µl; see Table 1) was added to each well and the plate was incubated for a further 24 hours. Absorbance at 570 nm of each sample was measured using a spectrophotometer (Dynatech MR7000).

(b) In vivo Administration (Closed Loop Rat Model).

In vivo rat closed loop studies were modified from the methods of Doluisio et al. [Doluisio J. T., et al: *Journal of Pharmaceutical Science* (1969), 58, 1196-1200] and Brayden et al. [Brayden D.: *Drug Delivery Pharmaceutical News* (1997) 4(1)]. Male Wistar rats (weight range 250 g-350 g) were anaesthetised with ketamine hydrochloride/acepromazine. A mid-line incision was made in the abdomen and a segment of the duodenum (7-9 cm of tissue) was isolated about 5 cm distal from the pyloric sphincter, taking care to avoid damage to surrounding blood vessels. The sample solutions (PBS containing C8 or C10 (35 mg) and TRH (500 µg and 1000 µg)) and control (PBS containing TRH only (500 µg and 1000 µg)) warmed to 37° C. were administered directly into the lumen of the duodenal segment using a 26 G needle. All intraduodenal dose volumes (for samples and control) were 1 ml/kg. The proximal end of the segment was ligated and the loop was sprayed with isotonic saline (37° C.) to provide moisture and then replaced in the abdominal cavity avoiding distension. The incision was closed with surgical clips. A group of animals were administered TRH in PBS (100 µg in 0.2 ml) by subcutaneous injection as a reference.

Figure 3:
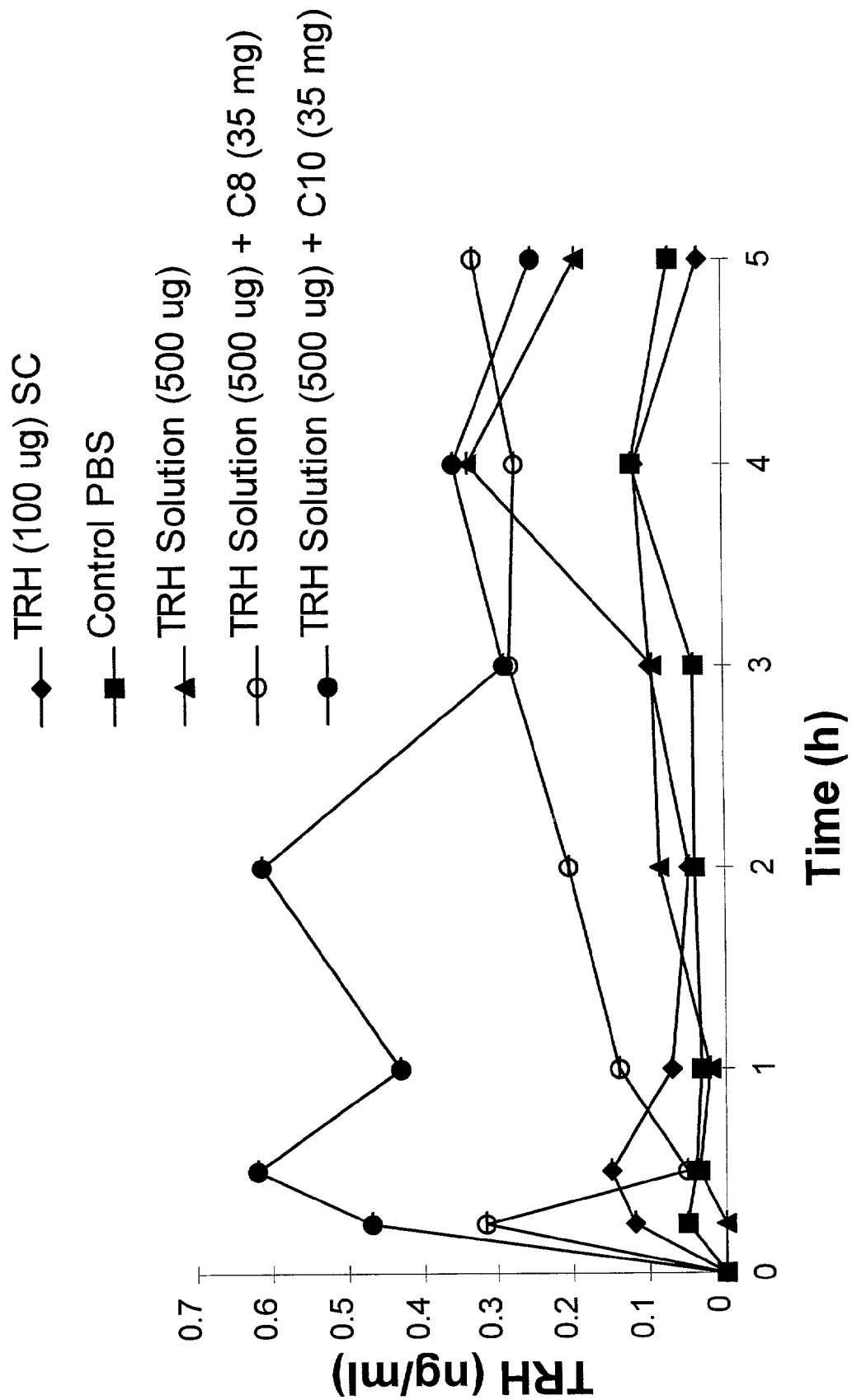
FIG. 3 shows the serum TRH concentration-time profiles following interduodenal bolus dose of 500 μg TRH with NaC8 or NaC10 (35 mg) enhancer present according to the closed loop rat model described in Example 1.
Figure 4:
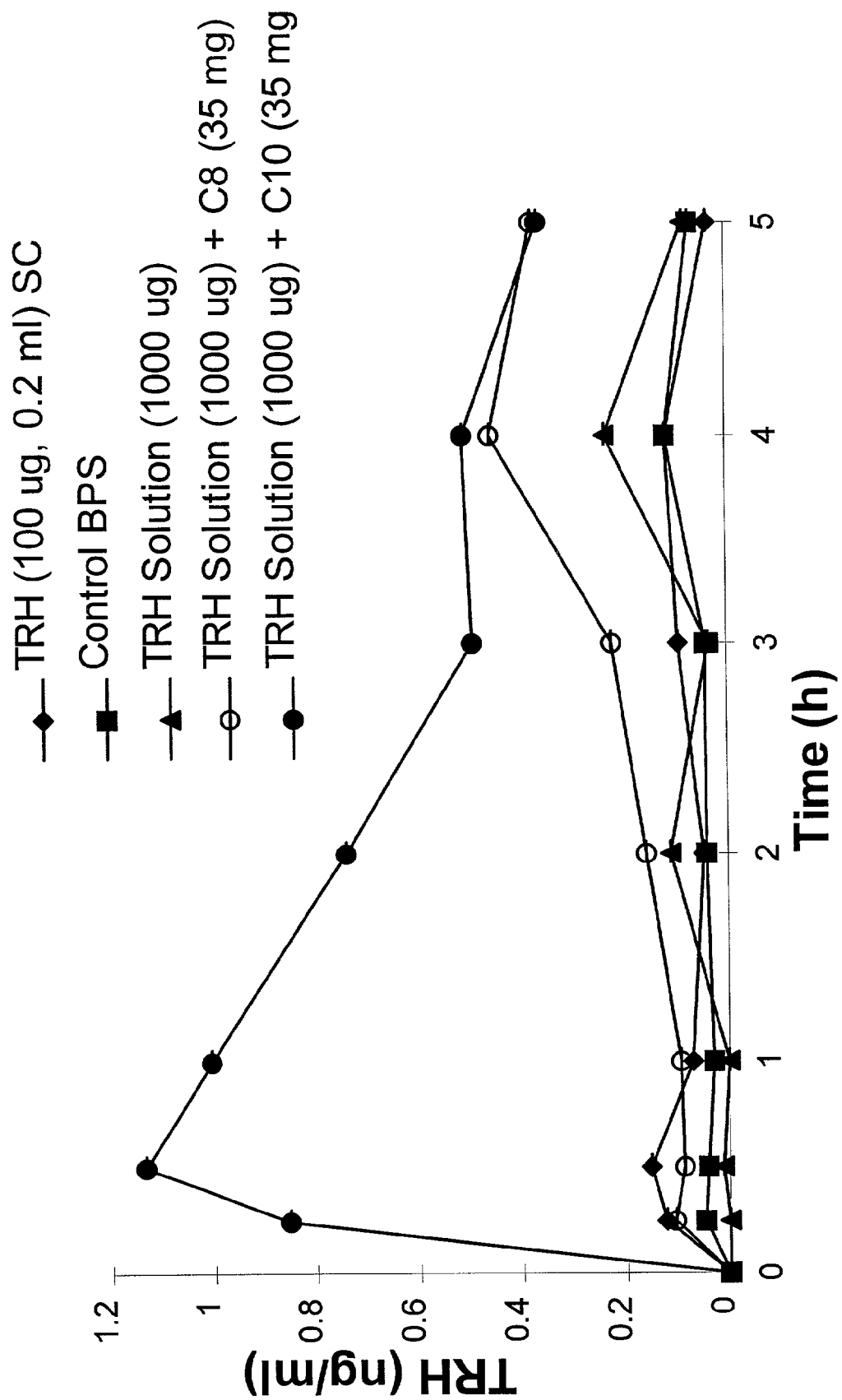
FIG. 4 shows the serum TRH concentration-time profiles following interduodenal bolus dose of 1000 μg TRH with NaC8 or NaC10 (35 mg) enhancer present according to the closed loop rat model described in Example 1.

FIG. 3 shows the serum TRH concentration-time profiles following interduodenal bolus dose of 500 µg TRH with NaC8 or NaC10 (35 mg) enhancer present, according to the closed loop rat model. FIG. 4 shows the serum TRH concentration-time profiles following interduodenal bolus dose of 1000 μg TRH with NaC8 or NaC10 (35 mg) enhancer present, according to the closed loop rat model. From FIGS. 3 and 4 it can be seen that the presence of the enhancer in each case significantly increases the serum levels of TRH over the control TRH solution indicating increased absorption of the drug in the presence of the enhancer.

(c) Tableting.

Having established the enhancing effect of NaC8 and NaC10 on TRH in solution, immediate release (IR) and sustained release (SR) TRH tablets and the like may be prepared. IR and SR formulations are detailed in Tables 2 and 3 below.

TABLE 2

THR IR tablet formulation details (all amounts in wt. %)

| TRH | NaC$_8$ | NaC$_{10}$ | Silica Dioxide | Mag. Stearate | Lactose | Disintegrant | Micro. Cellulose | PVP |
|---|---|---|---|---|---|---|---|---|
| 0.64 | 70.36 | — | 0.5 | 0.5 | 20 | 8 | — | — |
| 1.27 | 69.73 | — | 0.5 | 0.5 | 20 | 8 | — | — |
| 1.23 | — | 67.64 | 0.5 | 0.5 | 20 | 8 | — | 2.13 |
| 2.42 | — | 66.45 | 0.5 | 0.5 | — | 8 | 20 | 2.13 |
| 2.42 | — | 66.45 | 0.5 | 0.5 | 20 | 8 | — | 2.13 |

TABLE 3

THR SR tablet formulation details (all amounts in wt. %)

| TRH | NaC$_{10}$ | Silica Dioxide | Magnesium Stearate | HPMC[a] | Microcrystalline Cellulose | PVP |
|---|---|---|---|---|---|---|
| 1.41 | 77.59 | 0.5 | 0.5 | 20 | — | — |
| 1.05 | 57.95 | 0.5 | 0.5 | 20 | 20 | — |
| 2.68 | 73.94 | 0.5 | 0.5 | 20 | — | 2.37 |

EXAMPLE 2

Heparin Containing Tablets (a) Closed-loop Rat Segment.

Figure 5:
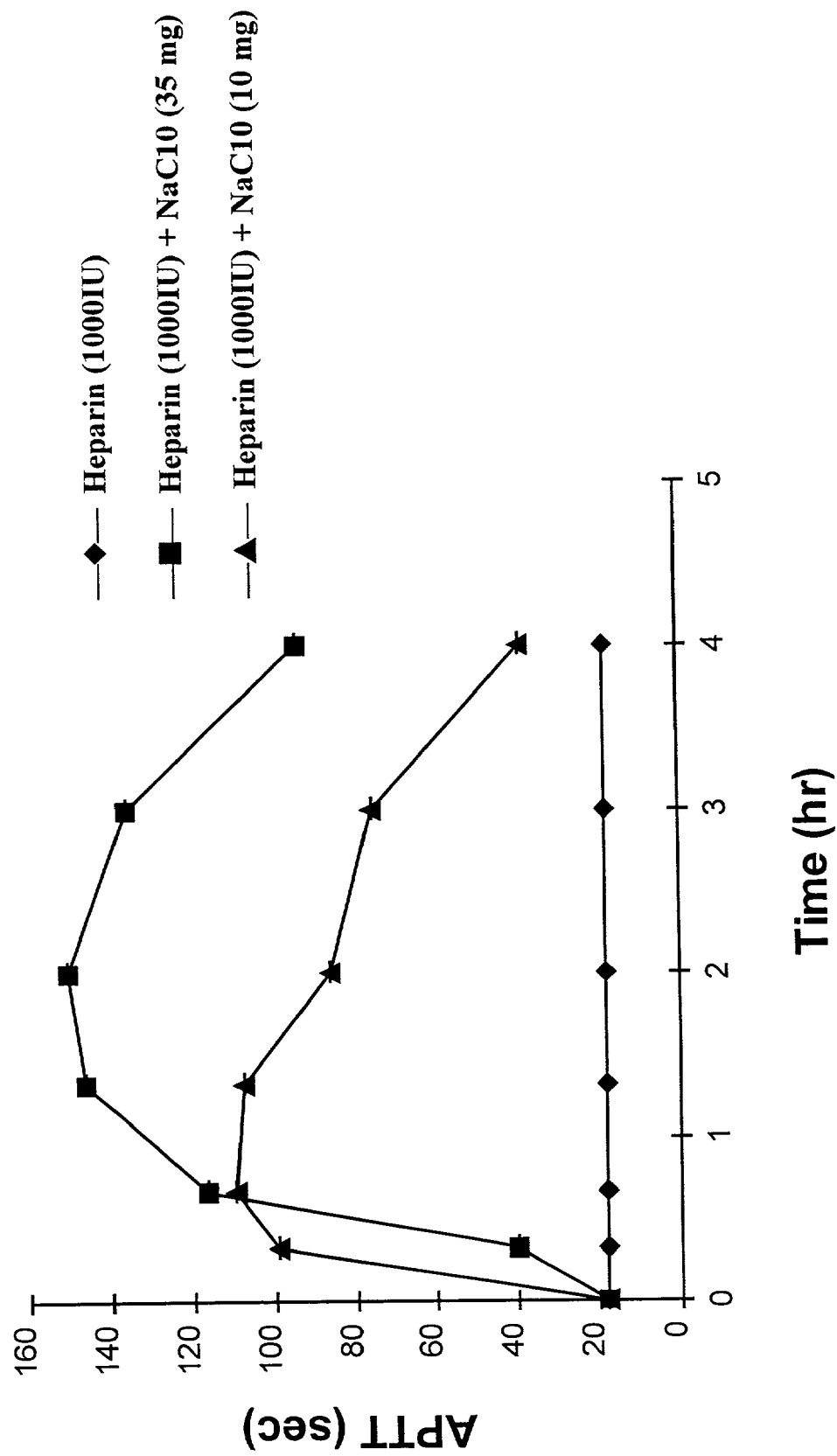
FIG. 5 shows the APTT response over a period of 4 hours following administration of USP heparin (1000 IU) with different sodium caprate (C10) levels (10 and 35 mg) according to the closed loop rat model described in Example 2.

The procedure carried out in Example 1 (a) above was repeated using USP heparin in place of TRH and dosing intraileally rather than intraduodenally. A mid-line incision was made in the abdomen and the distal end of the ileum located (about 10 cm proximal to the ileo-caecal junction). 7-9 cm of tissue was isolated and the distal end ligated, taking care to avoid damage to surrounding blood vessels. Heparin absorption as indicated by activated prothrombin time (APTT) response was measured by placing a drop of whole blood (freshly sampled from the tail artery) on the test cartridge of Biotrack 512 coagulation monitor. APTT measurements were taken at various time points. FIG. 5 shows the APTT response of USP heparin (1000 iu) at different sodium caprate (C10) levels (10 and 35 mg). Using APTT response as an indicator of heparin absorption into the bloodstream, it is clear that there is a significant increase in absorption in the presence of sodium caprate compared to the control heparin solution containing no enhancer.

Figure 6:
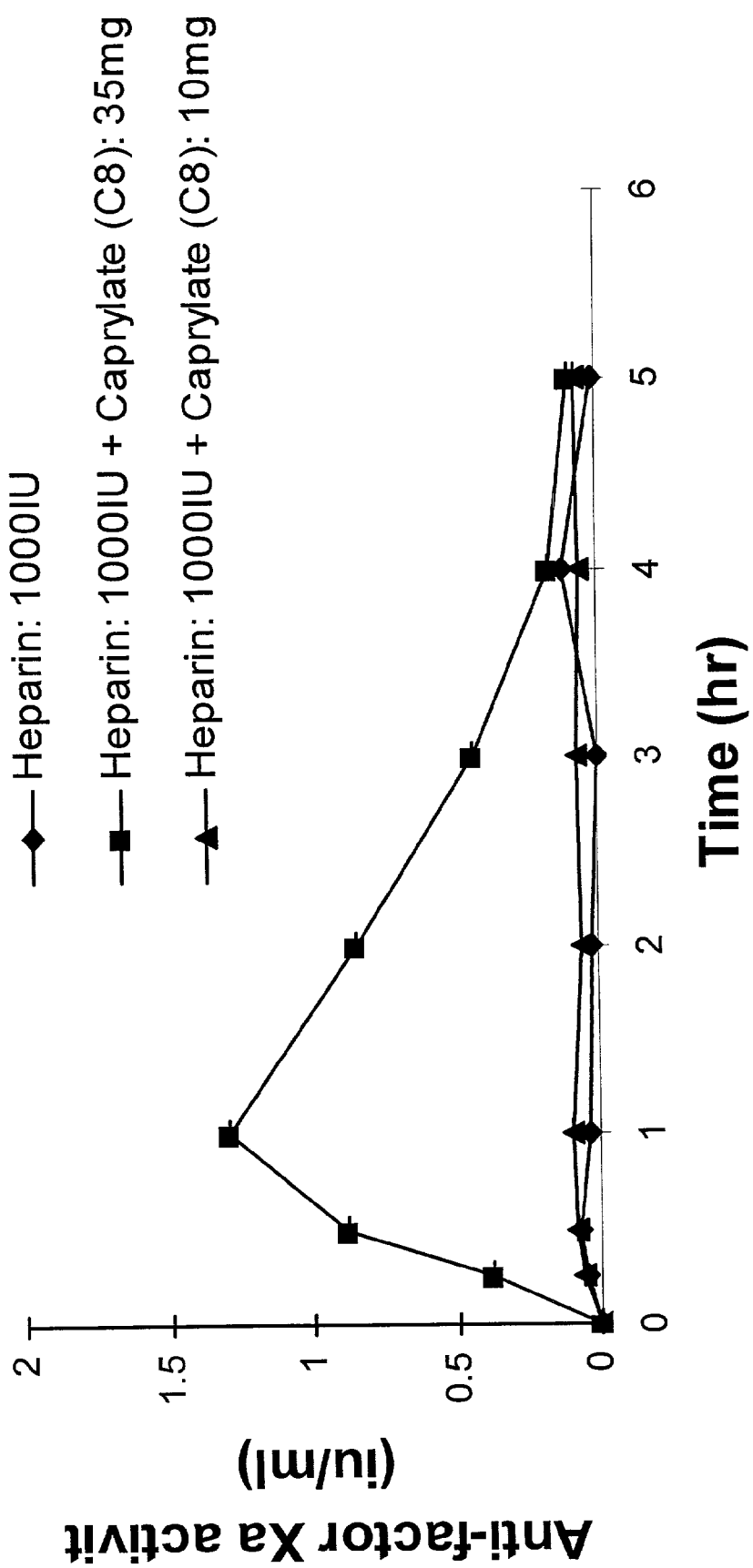
FIG. 6 shows the anti-factor Xa response over a period of 5 hours following administration of USP heparin (1000 IU) in the presence of different sodium caprylate (C8) levels (10 mg and 35 mg) according to the closed loop rat model described in Example 2.
Figure 7:
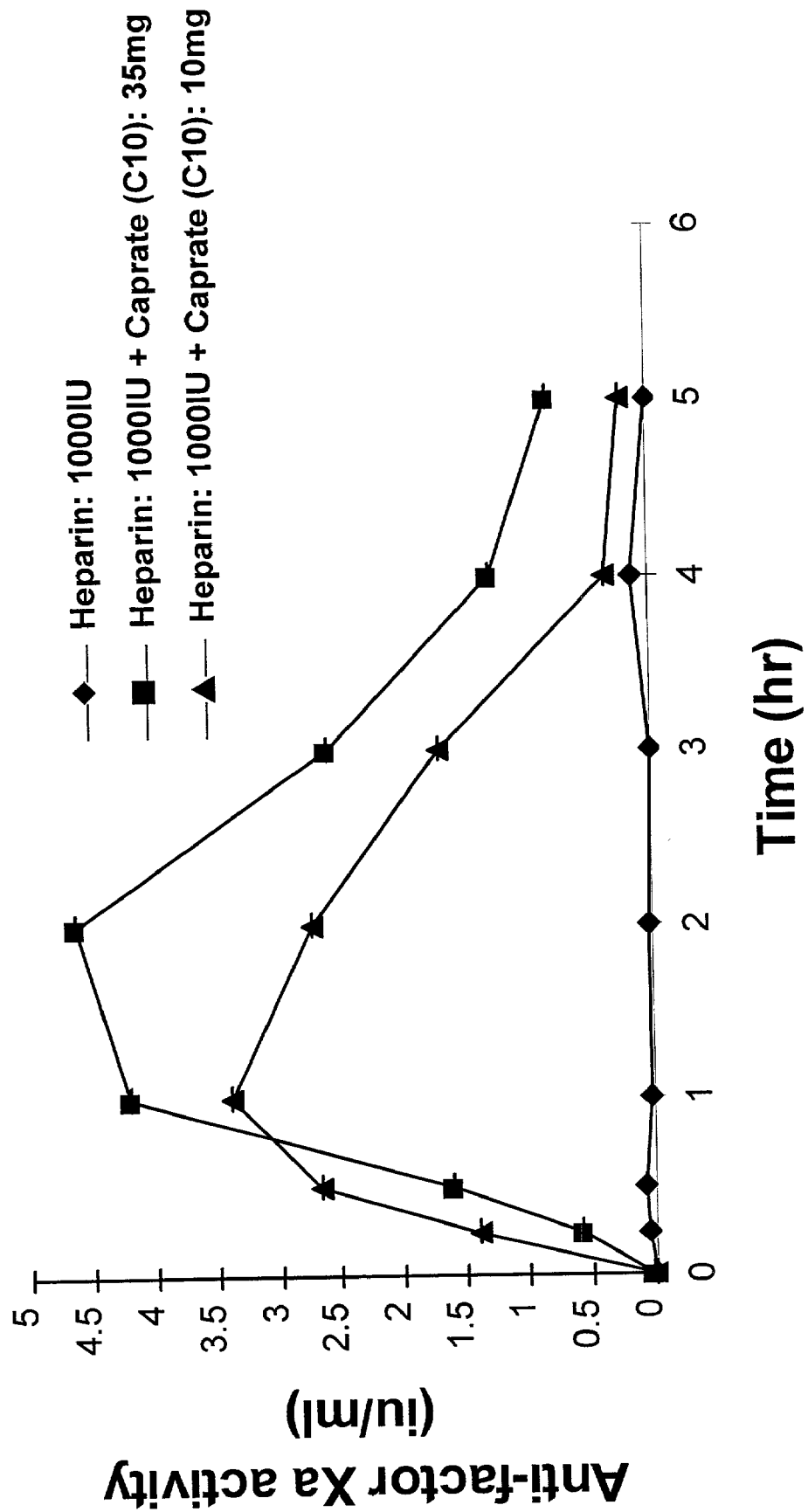
FIG. 7 shows the anti-factor Xa response over a period of five hours following administration of USP heparin (1000 IU) in the presence of different sodium caprate (C10) levels (10 mg and 35 mg) according to the closed loop rat model described in Example 2.

Citrated blood samples were centrifuged at 3000 rpm for 15 mins. to obtain plasma for anti-factor $X_a$ analysis. FIG. 6 shows the anti-factor $X_a$ response of USP heparin (1000 iu) in the presence of sodium caprylate (C8, 10 mg and 35 mg). FIG. 7 shows the anti-factor Xa response of USP heparin (1000 iu) in the presence of sodium caprate (C10, 10 mg and 35 mg). The control in each case is a solution of the same heparin concentration containing no enhancer. The significant increase in anti-factor $X_a$ activity observed for NaC8 (at 35 mg dose) and NaC10 (at both 10 mg and 35 mg doses) is indicative of the increase in heparin absorption relative to the control heparin solution containing no enhancer.

(b) Tableting.

(i) IR Tablets.

Instant release (IR) tablets containing heparin sodium USP (197.25 IU/mg, supplied by Scientific Protein Labs., Waunkee, Wis.) and an enhancer (sodium caprylate, NaC8; sodium caprate, NaC10, supplied by Napp Technologies, New Jersey) were prepared according to the formulae detailed in Table 4 by direct compression of the blend using a Manesty (E) single tablet press. The blend was prepared as follows: heparin, the enhancer and tablet excipients (excluding where applicable colloidal silica dioxide and magnesium stearate) were weighed out into a container. The colloidal silica dioxide, when present, was sieved through a 425 μm sieve into the container, after which the mixture was blended for four minutes before adding the magnesium stearate and blending for a further one minute.

TABLE 4

Formulation data for IR tablets containing heparin and enhancer (all amounts in wt. %)

| Batch No. | NaC$_8$ | NaC$_{10}$ | Heparin | Silica dioxide | Magnesium stearate | Mannitol | Disintegrant[a] | PVP[b] |
|---|---|---|---|---|---|---|---|---|
| 1 | 65.7 | — | 13.3 | 0.5 | 0.5 | 20.0 | — | — |
| 2 | 62.2 | — | 16.8 | 0.5 | 0.5 | 20.0 | — | — |
| 3 | 57.49 | — | 21.91 | 0.1 | 0.5 | 20.0 | — | — |
| 4 | 75.66 | — | 15.34 | 0.5 | 0.5 | — | 8.0 | — |
| 5 | — | 62.0 | 37.5 | 0.5 | — | — | — | — |
| 6 | — | 49.43 | 30.07 | 0.5 | — | 20.0 | — | — |
| 7 | — | 31.29 | 25.94 | 0.5 | 0.5 | 40.0 | — | 1.77 |

"—" indicates "not applicable";
[a] Disintegrant used was sodium starch glycolate;
[b] PVP = polyvinyl pyrrolidone The potency of tablets prepared above was tested using a heparin assay based on the azure dye determination of heparin. The sample to be assayed was added to an Azure A dye solution and the heparin content was calculated from the absorbance of the sample solution at 626 nm. Tablet data and potency values for selected batches detailed in Table 4 are given in Table 5.

Dissolution profiles for IR tablets according to this Example in phosphate buffer at pH 7.4 were determined by heparin assay, sampling at various time points.

Heparin/sodium caprylate: Tablets from batches 1 and 2 gave rapid release yielding 100% of the drug compound at 15 minutes. Tablets from batch 4 also gave rapid release yielding 100% release at 30 minutes.

Heparin/sodium caprate: Tablets from batches 5 and 6 gave rapid release 100% of the drug compound at 15 minutes.

Heparin/sodium caprylate: Dissolution data for batches 8, 9 and 11 are shown in Table 8. From this data it can be seen that heparin/sodium caprylate SR tablets with 15% Methocel K100LV with and without 5% sodium starch glycolate (batches 8 & 9) gave a sustained release with 100% release occurring between 3 and 4 hours. Batch 11 sustaining 10% mannitol gave a faster release.

Heparin/sodium caprate: Dissolution data for batches 13 and 14 are shown in Table 8. From this data it can be seen that heparin/sodium caprate SR tablets with 20% Methocel K100LV (batch 13) gave a sustained release of the drug compound over a six hour period. Where Methocel K15M (batch 14) was used in place of Methocel K100LV release of the drug compound was incomplete after 8 hours.

TABLE 5

Tablet data and potency values for IR heparin tablets

| Batch No. | Enhancer | Tablet weight (mg) | Hardness (N) | Disintegration time(s) | Actual heparin potency (mg/g) | Potency as % of label |
|---|---|---|---|---|---|---|
| 1 | $NaC_8$ | 431 ± 5 | 85 ± 4 | — | 145.67 | 109 |
| 2 | $NaC_8$ | 414 ± 14 | 82 ± 9 | — | 175.79 | 105 |
| 3 | $NaC_8$ | 650 ± 4 | 71 ± 12 | 552 | 166.4 | 119 |
| 4 | $NaC_8$ | 377 ± 2 | 58 ± 10 | — | 168.04 | 110 |
| 5 | $NaC_{10}$ | 408 ± 21 | 79 ± 7 | — | 394.47 | 105 |
| 6 | $NaC_{10}$ | 490 ± 6 | 124 ± 10 | — | 323.33 | 108 |
| 7 | $NaC_{10}$ | 584 ± 12 | 69 ± 22 | 485 | 143.0 | 102 |

(ii) SR Tablets.

Using the same procedure as used in (i) above, sustained release (SR) tablets were prepared according to the formulae shown in Table 6. The potency of controlled release tablets was determined using the same procedure as in (i) above. Tablet details and potency for selected batches are shown in Table 7.

Dissolution profiles for SR tablets according this Example were determined by heparin assay at pH 7.4, sampling at various time points.

TABLE 6

Formulation data for SR tablets containing heparin and enhancer (all amounts in wt. %)

| Batch No. | $NaC_8$ | $NaC_{10}$ | Heparin | Silica dioxide | Mag. stearate | HPMC[a] | Disintegrant[b] | Mannitol | Micro cellulose | PVP[c] |
|---|---|---|---|---|---|---|---|---|---|---|
| 8 | 69.84 | — | 14.16 | 0.5 | 0.5 | 15 | — | — | — | — |
| 9 | 65.68 | — | 13.32 | 0.5 | 0.5 | 15 | 5.0 | — | — | — |
| 10 | 65.68 | — | 13.32 | 0.5 | 0.5 | 12 | 8.0 | — | — | — |
| 11 | 65.68 | — | 13.32 | 0.5 | 0.5 | 10.0 | — | 10.0 | — | — |
| 12 | 53.77 | — | 20.48 | — | 1.0 | 14.85 | — | — | 9.9 | — |
| 13 | — | 56.2 | 23.3 | 0.5 | — | 20.0 | — | — | — | — |
| 14 | — | 56.2 | 23.3 | 0.5 | — | 20.0 | — | — | — | — |
| 15 | — | 41.63 | 34.52 | 0.5 | 1.0 | 20.0 | — | — | — | 2.35 |

"—"indicates "not applicable";
[a]Hydroxypropylmethyl cellulose: Methocel K100LV in each case except "*" in which Methocel K15M was employed;
[b]Disintegrant used was sodium starch glycolate;
[c]PVP = polyvinyl pyrrolidone;

TABLE 7

Table data and potency values for SR heparin tablets

| Batch No. | Enhancer | Tablet weight (mg) | Hardness (N) | Disintegration time (s) | Actual heparin potency (mg/g) |
|---|---|---|---|---|---|
| 8 | $NaC_8$ | 397 ± 5 | 52 ± 11 | — | — |
| 9 | $NaC_8$ | 436 ± 11 | 40 ± 10 | — | 140.08 |
| 10 | $NaC_8$ | 384 ± 4 | 42 ± 12 | — | — |

TABLE 7-continued

Table data and potency values for SR heparin tablets

| Batch No. | En-hancer | Tablet weight (mg) | Hardness (N) | Disintegration time (s) | Actual heparin potency (mg/g) |
|---|---|---|---|---|---|
| 11 | NaC$_8$ | 400 ± 8 | 72 ± 16 | — | 129.79 |
| 12 | NaC$_8$ | 683 ± 9 | 84 ± 17 | 3318 | 147.10 |
| 13 | NaC$_{10}$ | 491 ± 14 | 69 ± 7 | — | — |
| 14 | NaC$_{10}$ | 456 ± 13 | 47 ± 4 | — | — |
| 15 | NaC$_{10}$ | 470 ± 29 | — | 2982 | 148.20 |

TABLE 8

Dissolution data for selected batches of SR tablets

| | % Release (as % of label) | | | | |
|---|---|---|---|---|---|
| Time (min) | Batch 8 (NaC$_8$) | Batch 9 (NaC$_8$) | Batch 11 (NaC$_8$) | Batch 13 (NaC$_{10}$) | Batch 14 (NaC$_{10}$) |
| 0 | 0 | 0 | 0 | 0 | 0 |
| 15 | 22.9 | 21.2 | 45.3 | 18.8 | 5.7 |
| 30 | 37.3 | 30.8 | 72.3 | 45.0 | 11.6 |
| 60 | 57.8 | 54.5 | 101.9 | 44.8 | 11.2 |
| 120 | 92.2 | 90.8 | 109.4 | 65.2 | 20.0 |
| 240 | 109.5 | 105.8 | 96.4 | 83.1 | 33.9 |
| 360 | — | — | — | 90.3 | 66.0 |
| 480 | — | — | — | 102.7 | 82.8 |

(iii) Enteric Coated Tablets.

Tablets from batches 7 and 15 were enterically coated with a coating solution as detailed in Table 9. Tablets were coated with 5% w/w coating solution using a side vented coating pan (Freund Hi-Coata). Disintegration testing was carried out in a VanKel disintegration tester VK100E4635. Disintegration medium was initially simulated gastric fluid pH1.2 for one hour and then phosphate buffer pH7. The disintegration time recorded was the time from introduction into phosphate buffer pH7.4 to complete disintegration. The disintegration time for enterically coated tablets from batch 7 was 34 min. 24 sec, while for enteric coated tablets from batch 15 the disintegration time was 93 min. 40 sec.

TABLE 9

Enteric coating solution

| Component | Amount (wt. %) |
|---|---|
| Eudragit ® 12.5 | 49.86 |
| Diethyl phthlate | 1.26 |
| Isopropyl alcohol | 43.33 |
| Talc | 2.46 |
| Water | 3.06 |

(c) Dog Study.

Figure 8:
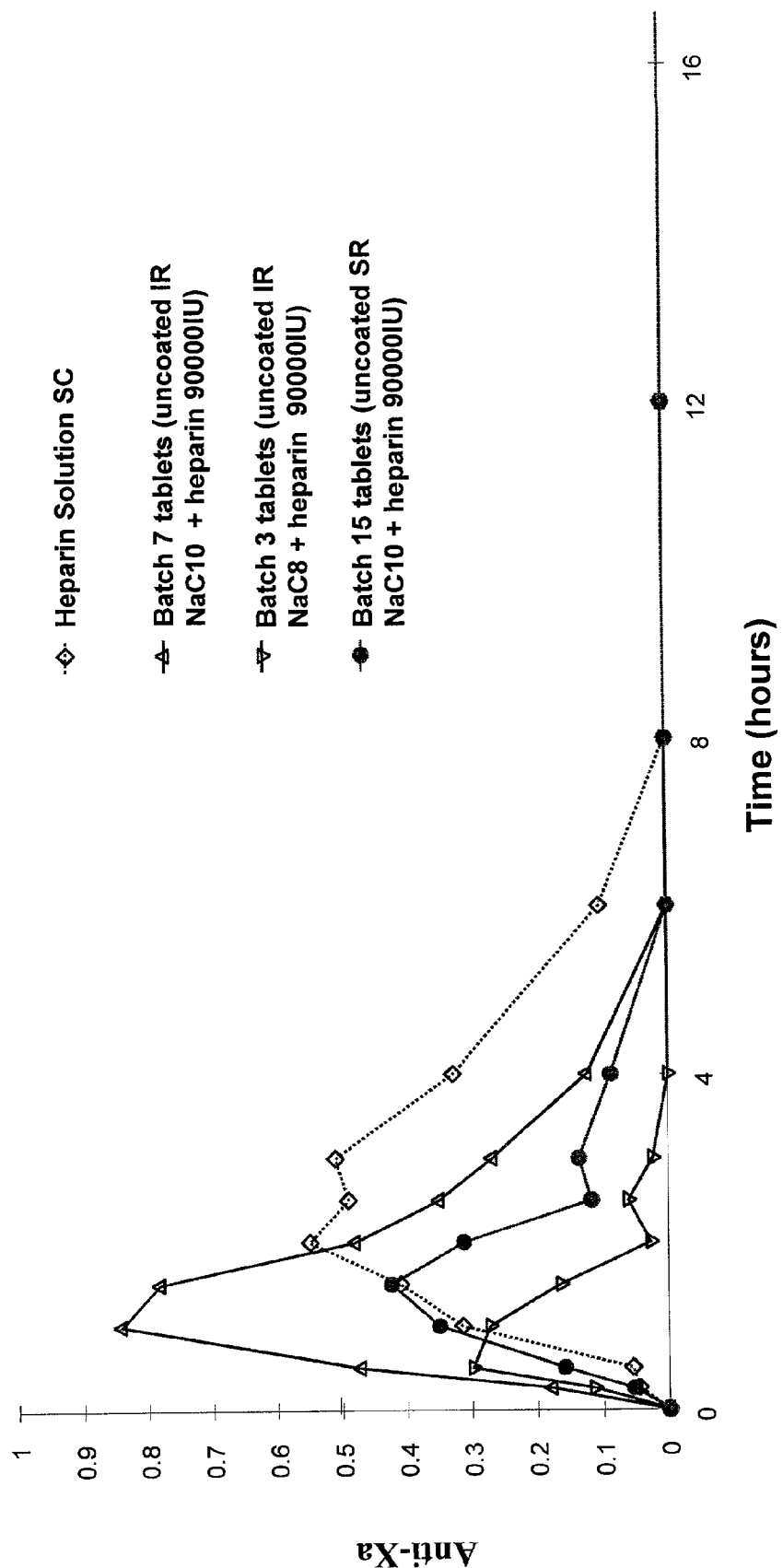
FIG. 8 shows the mean anti-factor Xa response in dogs over a period of time up to 8 hours following administration of: a) s.c. USP heparin solution (5000 IU); b) oral uncoated instant release tablet formulation containing USP heparin (90000 IU) and NaC10; c) oral uncoated instant release tablet formulation containing USP heparin (90000 IU) and NaC8; and d) oral uncoated sustained release tablet formulation containing USP heparin (90000 IU) and sodium caprate prepared according to the invention as described in Example 2.

Tablets from batches 3, 7 and 15 in Tables 5 and 6 above were dosed orally to groups of five dogs in a single dose crossover study. Each group was dosed with (1) orally administered uncoated IR tablets containing 90000 IU heparin and 550 mg NaC10 enhancer (batch 7); (2) orally administered uncoated IR tablets containing 90000 IU heparin and 550 mg NaC8 enhancer (batch 3); (3) orally administered uncoated SR tablets containing 90000 IU heparin and 550 mg NaC10 enhancer (batch 15) and (4) s.c. administered heparin solution (5000 IU, control). Blood samples for anti-factor Xa analysis were collected from the jugular vein at various times points. Clinical assessment of all animals pre- and post-treatment indicated no adverse effects on the test subjects. FIG. 8 shows the mean anti-factor X$_a$ response for each treatment, together with the s.c. heparin solution reference. The data in FIG. 8 shows an increase in the plasma anti-factor Xa activity for all of the formulations according to the invention. This result indicates the successful delivery of bioactive heparin using both NaC8 and NaC10 enhancers. Using IR formulations and an equivalent dose of heparin, a larger anti-factor Xa response was observed with the NaC10 enhancer, in spite of the lower dose of NaC10 relative to NaC8 administered (NaC10 dose was half that of NaC8). The anti-factor Xa response can be sustained over a longer time profile relative to the IR formulations by formulating as SR tablets.

EXAMPLE 3

Effect of Enhancers on the Systemic Availability of Low Molecular Weight Heparin (LMWH) after Intraduodenal Administration in Rats Male Wistar rats (250 g-350 g) were anaesthetised with a mixture of ketamine hydrochloride (80 mg/kg) and acepromazine maleate (3 mg/kg) given by intra-muscular injection. The animals were also administered with halothane gas as required. A midline incision was made in the abdomen and the duodenum was isolated.

The test solutions, comprising parnaparin sodium (LMWH) (Opocrin SBA, Modena, Italy) with or without enhancer reconstituted in phosphate buffered saline (pH 7.4), were administered (1 ml/kg) via a cannula inserted into the intestine approximately 10-12 cm from the pyloris. The intestine was kept moist with saline during this procedure. Following drug administration, the intestinal segment was carefully replaced into the abdomen and the incision was closed using surgical clips. The parenteral reference solution (0.2 ml) was administered subcutaneously into a fold in the back of the neck.

Figure 9:
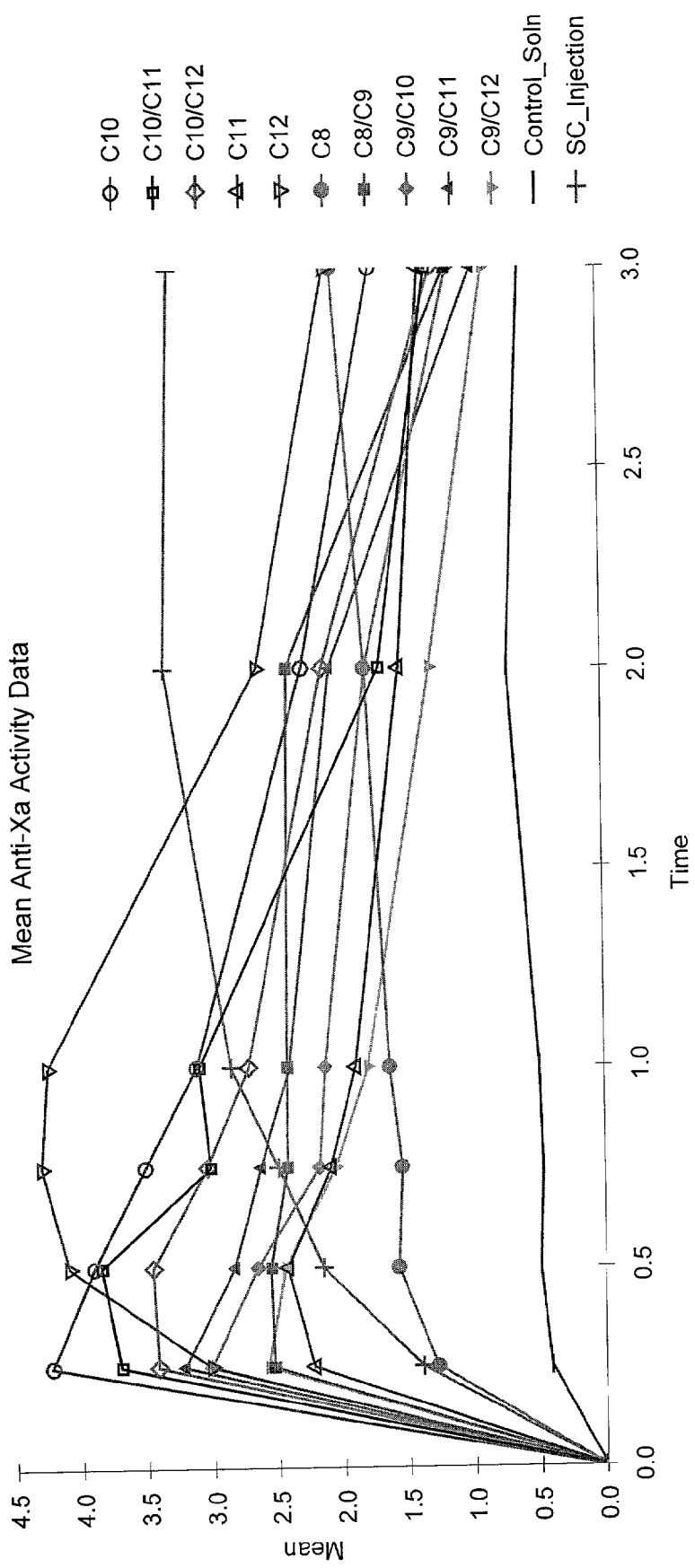
FIG. 9 shows the anti-factor Xa response over a period of three hours following intraduodenal administration to rats of phosphate buffered saline solutions of parnaparin sodium (low molecular weight heparin (LMWH)) (1000 IU), in the presence of 35 mg of different enhancers [sodium caprylate (C8), sodium nonanoate (C9), sodium caprate (C10), sodium undecanoate (C11), sodium laurate (C12)] and different 50:50 binary mixtures of enhancers, to rats (n=8) in an open loop model. The reference product comprised administering 250 IU parnaparin sodium subcutaneously. The control solution comprised administering a solution containing 1000 IU parnaparin sodium without any enhancer intraduodenally.

Blood samples were taken from a tail artery at various intervals and plasma anti-factor Xa activity was determined. FIG. 9 shows the mean anti-factor Xa response over a period of 3 hours following intraduodenal administration to rats of phosphate buffered saline solutions of parnaparin sodium (LMWH) (1000 IU), in the presence of 35 mg of different enhancers [sodium caprylate (C8), sodium nonanoate (C9), sodium caprate (C10), sodium undecanoate (C11), sodium laurate (C12)] and different 50:50 binary mixtures of enhancers, to rats (n=8) in an open loop model. The reference product comprised administering 250 IU parnaparin sodium subcutaneously. The control solution comprised administering a solution containing 1000 IU parnaparin sodium without any enhancer intraduodenally.

FIG. 9 shows that the systemic delivery of LMWH in the absence of enhancer is relatively poor after intraduodenal administration to rats; however, the co-administration of the sodium salts of medium chain fatty acids significantly enhanced the systemic delivery of LMWH from the rat intestine

EXAMPLE 4

Effect of Enhancers on the Systemic Availability of Leuprolide after Intraduodenal Administration in Dogs Beagle dogs (10-15 Kg) were sedated with medetomidine (80 µg/kg) and an endoscope was inserted via the mouth, oesophagus and stomach into the duodenum. The test solutions (10 ml), comprising leuprolide acetate (Mallinckrodt Inc, St. Louis, Mo.) with or without enhancer reconstituted in deionised water were administered intraduodenally via the endoscope. Following removal of the endoscope, sedation was reversed using atipamezole (400 μg/kg). The parenteral reference solutions comprising 1 mg Leuprolide reconstituted in 0.5 ml sterile water were administered intravenously and subcutaneously respectively.

Figure 10:
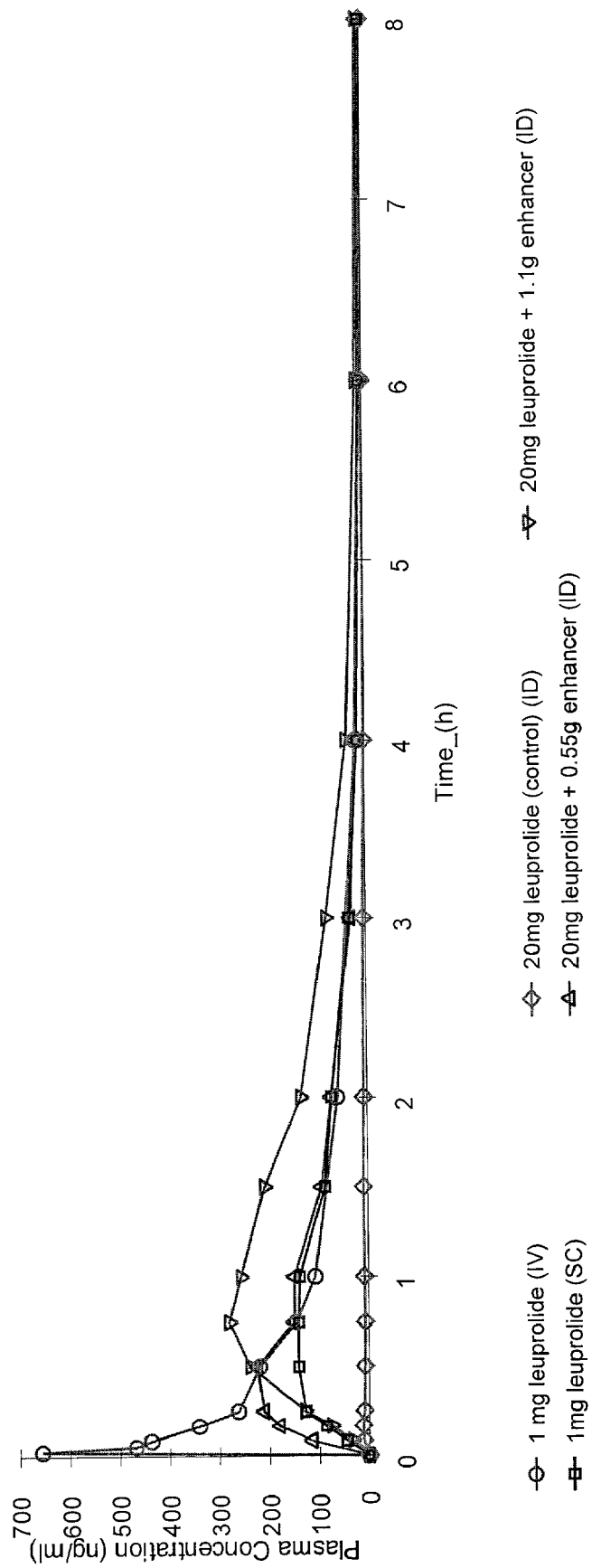
FIG. 10 shows the mean plasma levels of leuprolide over a period of eight hours following intraduodenal administration of solutions of leuprolide (20 mg) containing different levels of sodium caprate (0.0 g (control), 0.55 g, 1.1 g) to dogs.

Blood samples were taken from the jugular vein at various intervals and plasma leuprolide levels were determined. The resulting mean plasma leuprolide levels are shown in FIG. 10. The results show that, although the systemic delivery of leuprolide when administered intraduodenally without enhancer is negligible, coadministration with enhancer resulted in a considerable enhancer dose dependent enhancement in the systemic delivery of leuprolide; a mean % relative bioavailability of 8% observed for at the upper dose of enhancer.

EXAMPLE 5

Effect of Enhancers on the Systemic Availability of LMWH after Oral Administration in Dogs (a) Granulate Manufacture A 200 g blend containing parnaparin sodium (47.1%), sodium caprate (26.2%), mannitol (16.7%) and Explotab™ (Roquette Freres, Lestrem, France) (10.0%) was granulated in a Kenwood Chef mixer using water as the granulating solvent. The resulting granulates were tray dried in an oven at 67-68° C. and size reduced through 1.25 mm, 0.8 mm and 0.5 mm screens respectively in an oscillating granulator. The actual potency of the resulting granulate was determined as 101.1% of the label claim.

(b) 30,000 IU LMWH/183 mg Sodium Caprate Instant Release Tablet Manufacture

The granulate described above was bag blended with 0.5% magnesium stearate for 5 minutes. The resulting blend was tabletted using 13 mm round concave tooling on a Riva Piccalo tablet press to a target tablet content of 30,000 IU parnaparin sodium and 183 mg sodium caprate. The tablets had a mean tablet hardness of 108 N and a mean tablet weight of 675 mg. The actual LMWH content of the tablets was determined as 95.6% of label claim.

Disintegration testing was carried out on the tablets. One tablet was placed in each of the six tubes of the disintegration basket. The disintegration apparatus was operated at 29-30 cycles per minute using de-ionised water at 37° C. Tablet disintegration was complete in 550 seconds.

(c) 90,000 IU LMWH/0.55 g Sodium Caprate Solution Manufacture 90,000 IU parnaparin sodium and 0.55 g sodium caprate were individually weighed into glass bottles and the resulting powder mixture was reconstituted with 10 ml water.

(d) Dog Biostudy Evaluation 90,000 IU parnaparin sodium and 550 mg sodium caprate was administered as both a solution dosage form (equivalent to 10 ml of the above solution composition) and a fast disintegrating tablet dosage form (equivalent to 3 tablets of the above tablet composition) in a single dose, non randomised, cross-over study in a group of six female beagle dogs (9.5-14.4 Kg) with a seven day washout between treatments. A subcutaneous injection containing 5000 IU parnaparin sodium was used as the reference.

Figure 11:
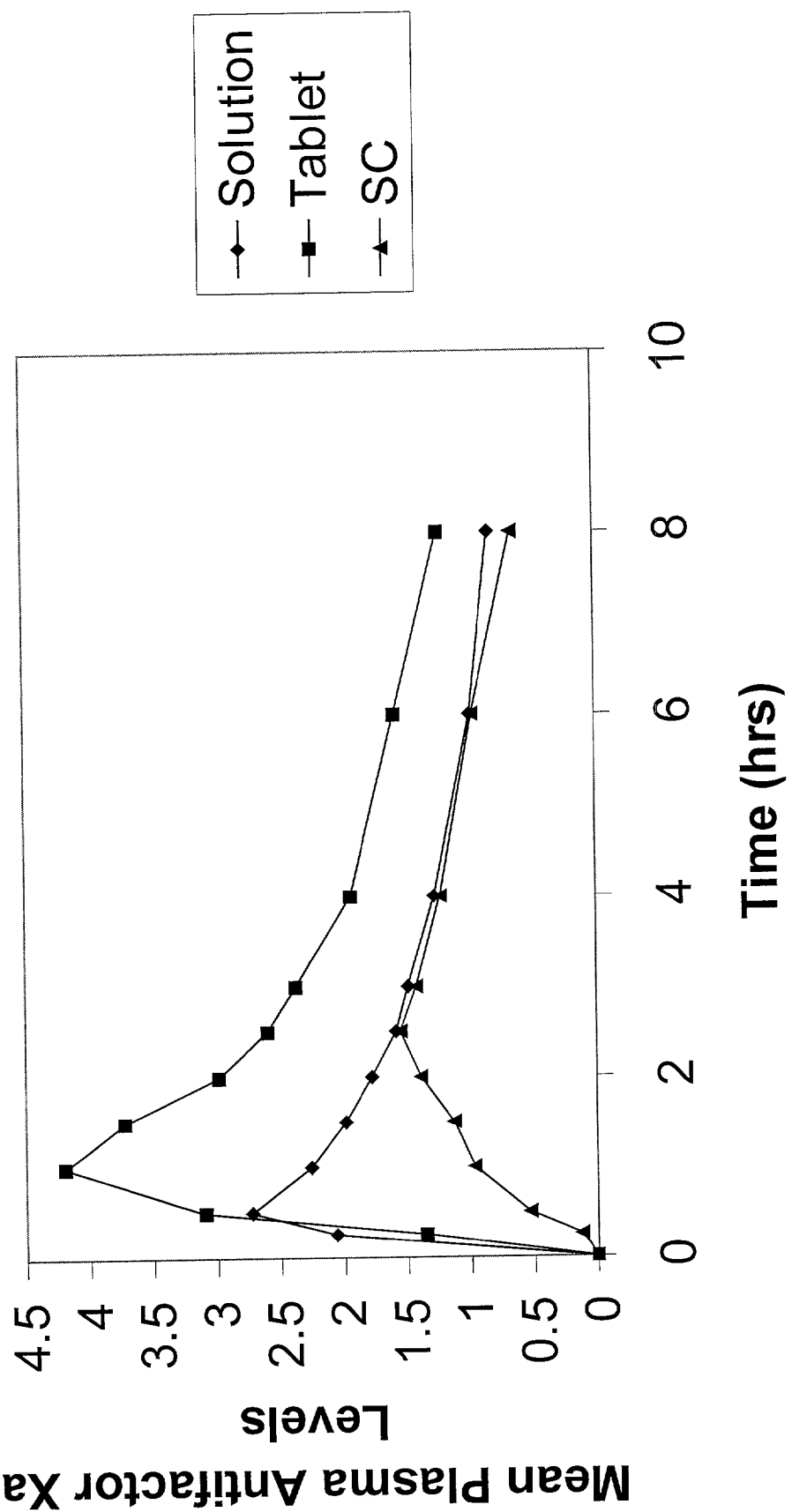
FIG. 11 shows the mean anti-factor Xa response in dogs over a period of eight hours following oral administration of parnaparin sodium (90,000 IU) in the presence of 550 mg sodium caprate, as both a solution (10 ml) and an instant release tablet dosage form.

Blood samples were taken from the jugular vein at various intervals and anti-factor Xa activity was determined. Data was adjusted for baseline anti-factor Xa activity. The resulting mean plasma anti-factor Xa levels are summarised in FIG. 11. Both the tablet and solution dosage forms showed good responses when compared with the subcutaneous reference leg. The mean delivery, as determined by plasma antifactor Xa levels, of parnaparin sodium from the solid dosage form was considerably greater than that from the corresponding solution dosage form.

EXAMPLE 6

Effect of Enhancers on the Systemic Availability of LMWH after Oral Administration in Humans (a) Granulate Manufacture Parnaparin sodium (61.05%), sodium caprate (33.95%) and polyvinyl pyrrolidone (Kollidon 30, BASF AG, Ludwigshafen, Germany) (5.0%) were mixed for 5 minutes in a Gral 10 prior to the addition of water, which was then gradually added, with mixing, using a peristaltic pump until all the material was apparently granulated.

The resultant granulates were tray dried in an oven at either 50° C. for 24 hours. The dried granules were milled through a 30 mesh screen using a Fitzmill M5A (b) 45,000 IU LMWH/275 mg Sodium Caprate Instant Release Tablet Manufacture The parnaparin sodium/sodium caprate/polyvinyl pyrrolidone granulate (78.3%) was blended for 5 minutes with mannitol (16.6%), explotab (5.0%) and magnesium stearate (1.0%) in a 10 litre V Cone blender. The potency of the resulting blend (480.41 mg/g) was 100.5% of the label claim.

The blend was tabletted using 13 mm round normal concave tooling on the Piccola 10 station press in automatic mode to a target content of 45,000 IU LMWH and 275 mg sodium caprate. The resulting instant release tablets had a mean tablet weight of 1027 mg, a mean tablet hardness of 108 N and a potency of 97% label claim. The tablets showed a disintegration time of up to 850 seconds and 100% dissolution into pH 1.2 buffer in 30 minutes.

(c) 90,000 IU LMWH/550 mg Sodium Caprate Solution Manufacture

Two instant tablets, each containing 45,000 IU LMWH and 275 mg sodium caprate, were reconstituted in 30 ml water.

(d) Human Biostudy Evaluation 90,000 IU LMWH and 550 mg sodium caprate was orally administered to 12 healthy human volunteers as both a solution dosage form (equivalent to 30 ml of the above solution dosage form) and as a solid dosage form (equivalent to 2 tablets of the above composition) in an open label, three treatment, three period study with a seven day washout between each dose; Treatments A (Instant Release Tablets) and B (Oral Solution) were crossed over in a randomised manner whereas Treatment C (6,400 IU Fluxum™ SC (Hoechst Marion Roussel), a commercially available injectable LMWH product) was administered to the same subjects as a single block.

Figure 12:
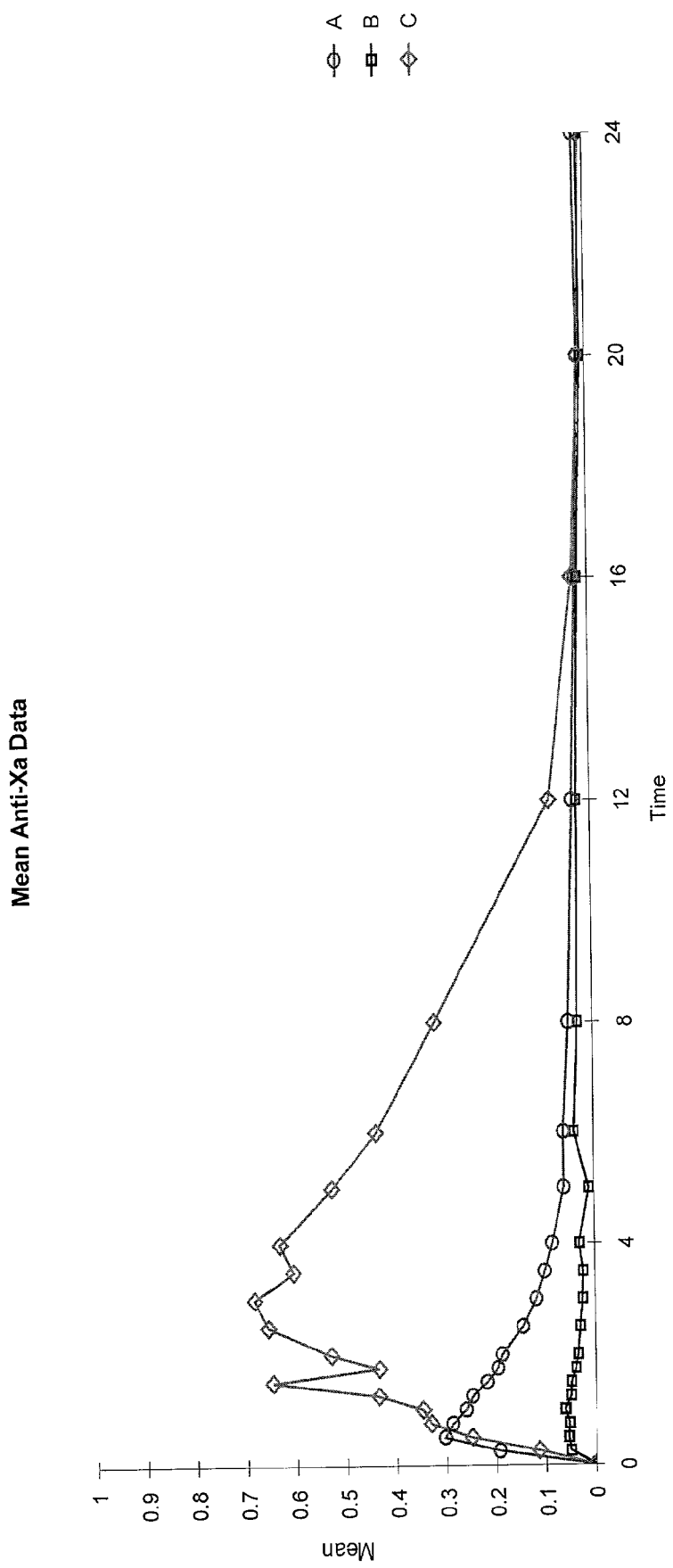
FIG. 12 shows the mean anti-factor Xa response in humans over a period of 24 hours following oral administration of parnaparin sodium (90,000 IU) in the presence of sodium caprate, as both a solution (240 ml) and an instant release tablet dosage form

Blood samples were taken at various intervals and antifactor X a activity was determined. The resulting mean antifactor Xa levels are shown in FIG. 12. Treatments A and B exhibited unexpectedly low responses when compared with the subcutaneous reference treatment. However it should be noted that the mean delivery of LMWH, as measured by plasma anti-factor Xa levels, was considerably higher from the solid dosage form than that from the corresponding solution dosage form for which a mean % bioavailability of only 0.9% was observed.

EXAMPLE 7

Figure 13:
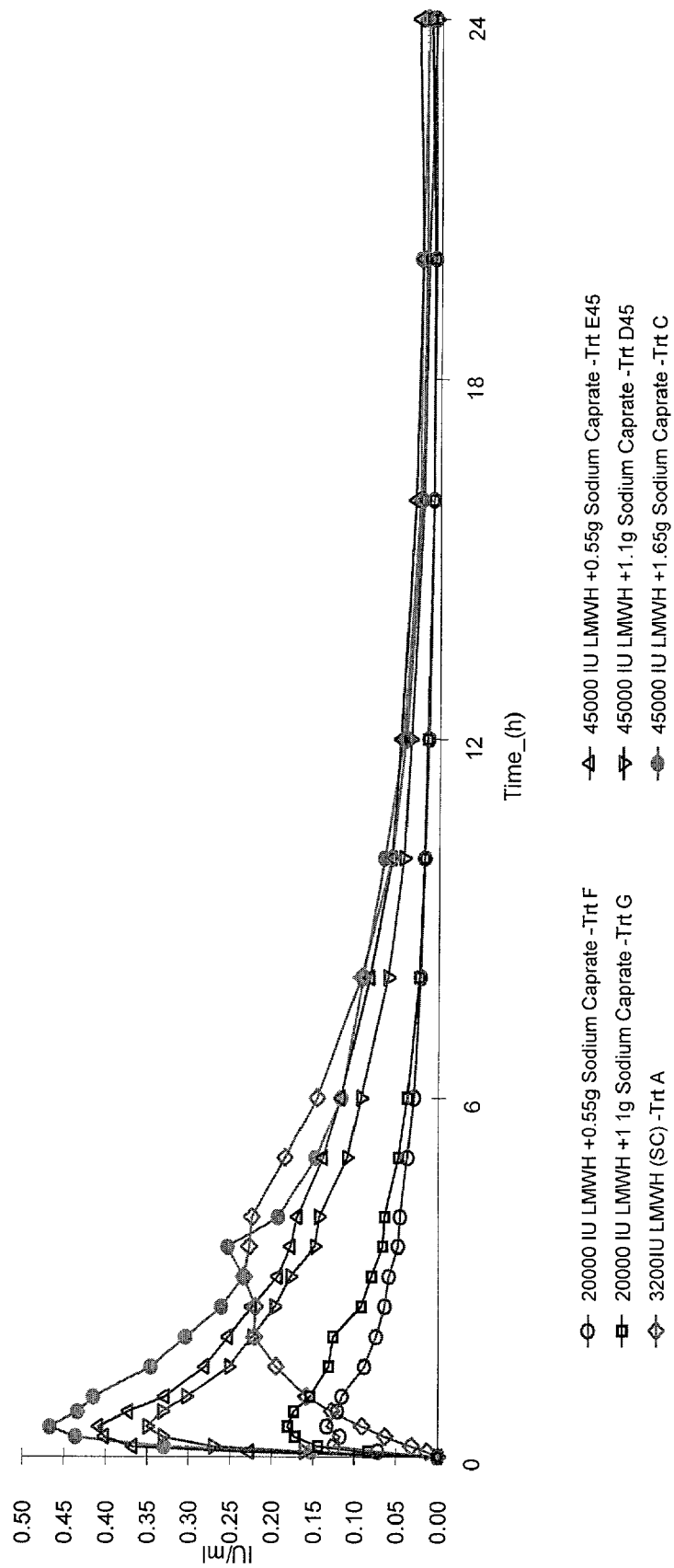
FIG. 13 shows the mean anti-factor Xa response in humans over a period of 24 hours following intrajejunal administration of 15 ml solutions containing different doses parnaparin sodium (20,000 IU, 45,000 IU, 90,000 IU) in the presence of different doses of sodium caprate (0.55 g, 1.1 g, 1.65 g)

Effect of Enhancers on the Systemic Availability of LMWH after Intrajejunal Administration in Humans (a) Solution Manufacture The following LMWH/sodium caprate combinations were made with 15 ml deionised water:
 (i) 20,000 IU LMWH, 0.55 g Sodium Caprate;
 (ii) 20,000 IU LMWH, 1.1 g Sodium Caprate;
 (iii) 45,000 IU LMWH, 0.55 g Sodium Caprate;
 (iv) 45,000 IU LMWH, 1.1 g Sodium Caprate;
 (v) 45,000 IU LMWH, 1.65 g Sodium Caprate (b) Human Biostudy Evaluation 15 ml of each of the above solutions was administered intrajejunally via a nasojejunal intubation in an open label, six treatment period crossover study in up to 11 healthy human volunteers. 3,200 IU Fluxum™ SC was included in the study as a subcutaneous reference. Blood samples were taken at various intervals and anti-factor X a activity was determined. The resulting mean anti-factor Xa levels are shown in FIG. 13.

It should be noted that the mean % relative bioavailability for each treatment in the current study was considerably higher than the mean % bioavailability observed for the solution dosage form in Example 6; mean % bioavailabilities ranging from 5% to 9% were observed for the treatments in the current study suggesting that the preferred LMWH oral dosage form containing sodium caprate should be designed to minimise release of drug and enhancer in the stomach and maximise the release of drug and enhancer in the small intestine.

EXAMPLE 8

Manufacture of Delayed Release Tablet Dosage Form Containing LMWH and Enhancer (a) LMWH/Sodium Caprate Granulate Manufacture A 500 g batch of parnaparin sodium:sodium caprate (0.92:1) was granulated in a Gral 10 using a 50% aqueous solution of Kollidon 30 as the granulating solvent. The resulting granulate was dried for 60 minutes in a Niro Aeromatic Fluidised Bed Drier at a final product temperature of 25° C. The dried granulate was milled through a 30 mesh screen in a Fitzmill M5A. The potency of the resulting dried granulate was determined as 114.8% of the label claim.

(b) 22,500 IU LMWH/275 mg Sodium Caprate Instant Release Tablet Manufacture

The above granulate (77.5%) was added to mannitol (16%), Polyplasdone™ XL (ISP, Wayne, N.J.) (5%) and Aerosil™ (1%) (Degussa, Rheinfelden, Germany)in a 10 IV coned blender and blended for 10 minutes. Magnesium stearate (0.5%) was added to the resulting blend and blending was continued for a further 3 minutes.

The resulting blend was tabletted on Piccola tablet press using 13 mm round normal concave tooling to a mean tablet weight of 772 mg and a mean tablet hardness of 140 N.

The actual potency of the resulting tablets was determined as 24,017 IU LMWH per tablet.

(c) 22,500 IU LMWH/275 mg Sodium Caprate Delayed Release Tablet Manufacture

The above tablets were coated with a coating solution containing Eudragit L 12.5 (50%), isopropyl alcohol (44.45%), dibutyl sebecate (3%), talc (1.3%), water (1.25%) in a Hicoater to a final % weight gain of 5.66%.

The resulting enteric coated tablets remained intact after 1 hour disintegration testing in pH 1.2 solution; complete disintegration was observed in pH 6.2 medium after 32-33 minutes.

EXAMPLE 9

Manufacture of Instant Release Capsule Dosage Form Containing LMWH and Enhancer (a) 22,500 IU LMWH/275 mg Sodium Caprate Instant Release Capsule Manufacture The granulate from the previous example, part a, was hand filled into Size 00 hard gelatin capsules to a target fill weight equivalent to the granulate content of the tablets in the previous example.

EXAMPLE 10

Manufacture of Delayed Release Tablet Dosage Form Containing LMWH without Enhancer (a) LMWH Granulate Manufacture A 500 g batch of parnaparin sodium: Avicel™ pH 101 (0.92:1) (FMC, Little Island, Co. Cork, Ireland) was granulated in a Gral 10 using a 50% aqueous solution of Kollidon 30 as the granulating solvent. The resulting granulate was dried for 60 minutes in a Niro Aeromatic Fluidised Bed Drier at an exhaust temperature of 38° C. The dried granulate was milled through a 30 mesh screen in a Fitzmill M5A. The potency of the resulting dried granulate was determined as 106.5% of the label claim.

(b) 22,500 IU LMWH Instant Release Tablet Manufacture

The above granulate (77.5%) was added to mannitol (21%) and aerosil (1%) in a 25 L V coned blender and blended for 10 minutes. Magnesium stearate (0.5%) was added to the resulting blend and blending was continued for a further 1 minute.

The resulting blend was tabletted on Piccola tablet press using 13 mm round normal concave tooling to a mean tablet weight of 671 mg and a mean tablet hardness of 144 N.

The actual potency of the resulting tablets was determined as 21,651 IU LMWH per tablet.

(c) 22,500 IU LMWH Delayed Release Tablet Manufacture

The above tablets were coated with a coating solution containing Eudragit L 12.5 (50%), isopropyl alcohol (44.45%), dibutyl sebecate (3%), talc (1.3%) and water (1.25%) in a Hicoater to a final % weight gain of 4.26%.

The resulting enteric coated tablets remained intact after 1 hour disintegration testing in pH 1.2 solution; complete disintegration was observed in pH 6.2 medium in 22 minutes.

EXAMPLE 11

Effect of Controlled Release Dosage Form Containing Enhancer on the Systemic Availability of LMWH after Oral Administration in Dogs (a) Dog Study Evaluation 45,000 IU LMWH was administered to 8 beagle dogs (10.5-13.6 Kg), in an open label, non randomised crossed over block design, as (a) an instant release capsule dosage form containing 550 mg sodium caprate (equivalent to 2 capsules manufactured according to Example 9) (b) a delayed release tablet dosage containing 550 mg sodium caprate (equivalent to two tablets manufactured according to Example 8) and (c) a delayed release tablet dosage not containing any enhancer (equivalent to 2 tablets manufactured according to Example 10). 3,200 IU Fluxum™ SC was included in the study as a subcutaneous reference.

Figure 14:
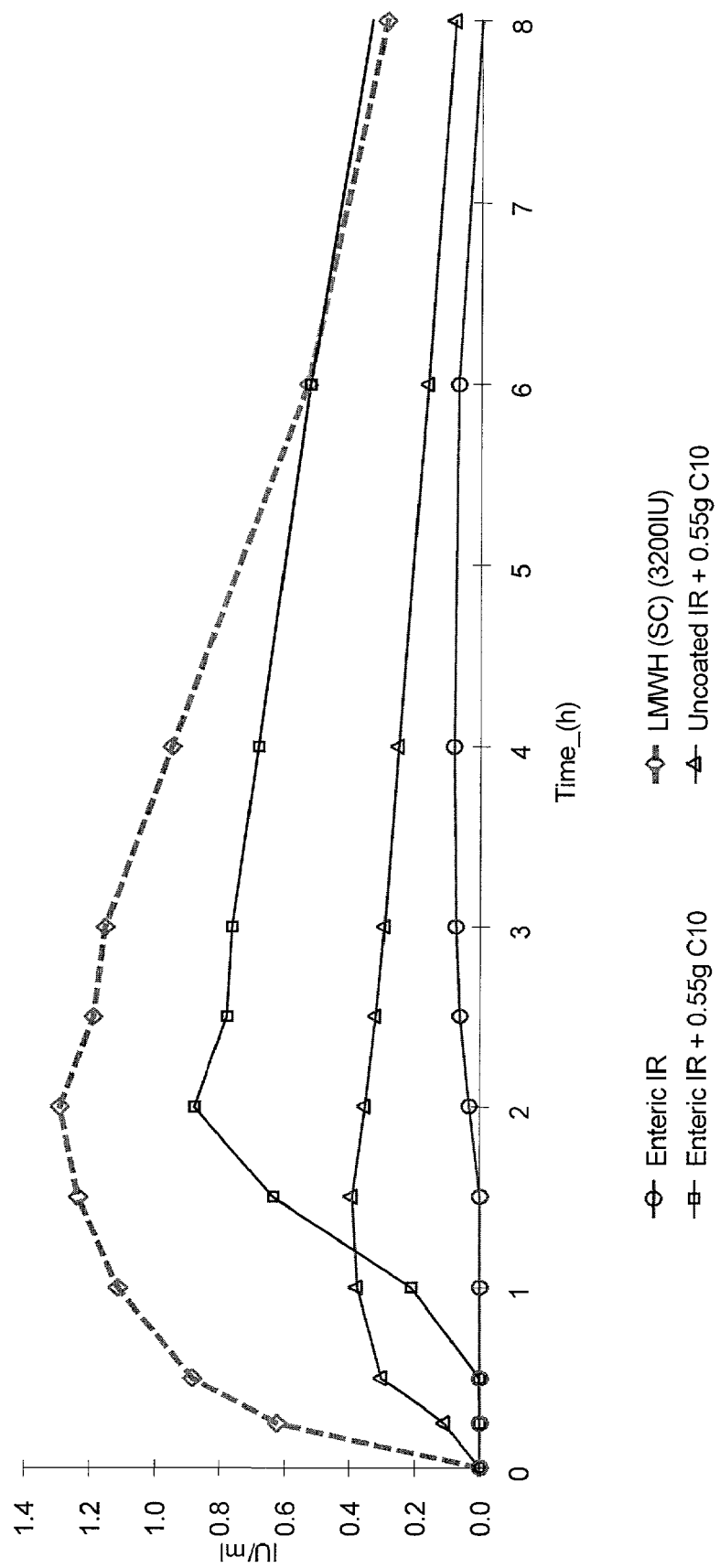
FIG. 14 shows the mean anti-factor Xa response in dogs over a period of 8 hours following oral administration of 45,000 IU parnaparin sodium as: (a) instant release capsules containing 0.55 g sodium caprate, (b) Eudragit L coated rapidly disintegrating tablets containing 0.55 g sodium caprate and (c) Eudragit L coated rapidly disintegrating tablets without enhancer.

Blood samples were taken from the jugular vein at various intervals and anti-factor X a activity was determined. The resulting mean anti-factor Xa levels are shown in FIG. 14.

It should be noted that in the absence of sodium caprate, the systemic delivery of LMWH was minimal from the delayed release solid dosage form without enhancer. In contrast, a good anti-factor Xa response was observed after administration of the delayed release LMWH solid dosage form containing sodium caprate. The mean anti-factor Xa response from the delayed release dosage form containing sodium caprate was considerably higher than that from the instant release dosage form containing the same level of drug and enhancer.

EXAMPLE 12

Effect of the Site of Administration on the Systemic Availability of LMWH in Dogs after Co-administration with Enhancer Four beagle dogs (10-15 Kg) were surgically fitted with catheters to the jejunum and colon respectively. The test solutions (10 ml) comprising LMWH with sodium caprate reconstituted in deionised water were administered to the dogs either orally or via the intra-intestinal catheters. 3,200 IU Fluxum™ SC was included in the study as a subcutaneous reference.

Figure 15:
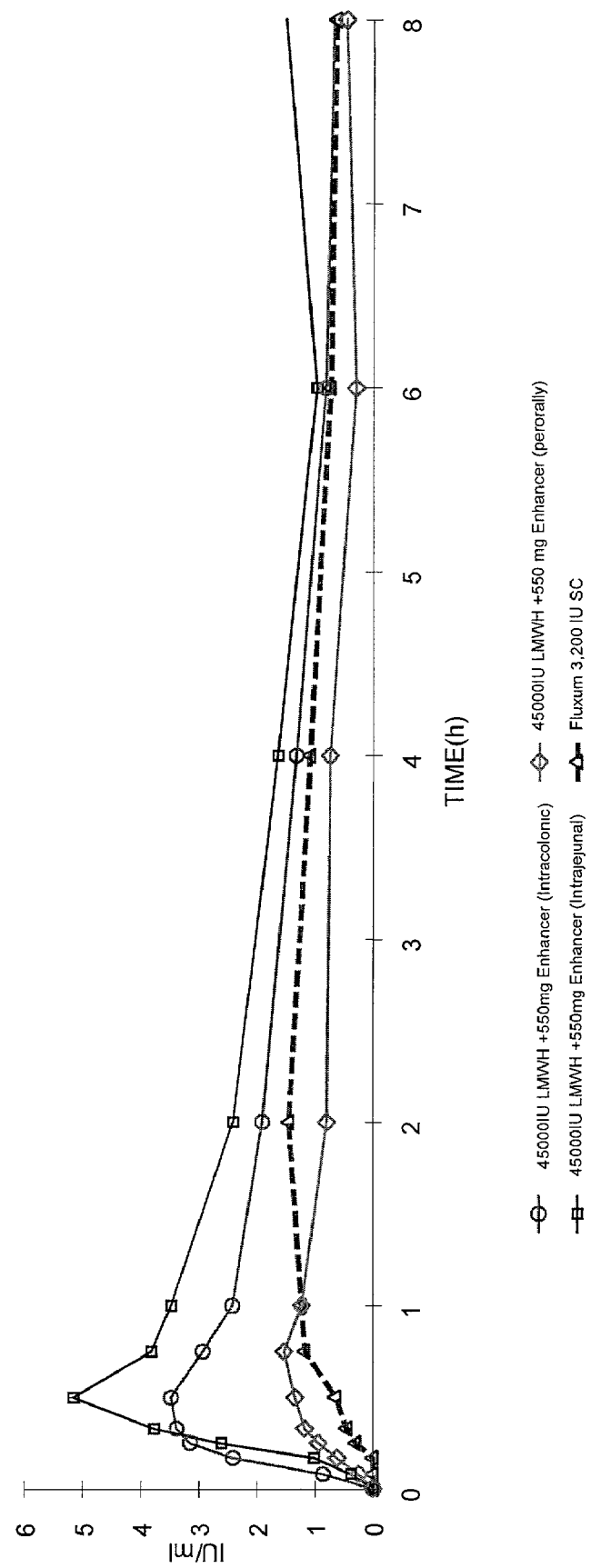
FIG. 15 shows the mean anti-factor Xa response in dogs over a period of 8 hours following co-administration of 45,000 IU LMWH and 0.55 g sodium caprate orally, intrajejunally and intracolonically compared to subcutaneous administration.

Blood samples were taken from the brachial vein at various intervals and anti-factor Xa activity was determined. The resulting mean anti-factor Xa levels are shown in FIG. 15. The results show that the intestinal absorption of LMWH in the presence of enhancer is considerably higher than absorption from the stomach.

EXAMPLE 13

Leuprolide Containing Tablets

Following the same type of approach as used in Examples 1 and 2, leuprolide-containing IR tablets may be prepared according to the formulations detailed in Table 10.

TABLE 10

IR tablet formulations containing Leuprolide (all amounts in wt. %)

| Leuprolide | NaC10 | Silica Dioxide | Magnesium Stearate | Lactose | Disintegrant | Microcystalline Cellulose |
|---|---|---|---|---|---|---|
| 0.05 | 68.82 | 0.5 | 0.5 | 20 | 8 | — |
| 0.13 | 70.87 | 0.5 | 0.5 | — | 8 | 20 |
| 0.13 | 68.75 | 0.5 | 0.5 | 20 | 8 | — |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A solid oral dosage form which is effective in delivering a drug and an enhancer, each as defined below, to an intestine and which comprises a pharmaceutical composition consisting of:

(A) a therapeutically effective amount of a bisphosphonate drug in the form of crystalline and/or amorphous particles;
(B) one or more absorption enhancers, each of which: (i) is a solid at room temperature; (ii) is a salt of a medium chain fatty acid having a carbon length of from 8 to 14 carbon atoms in particulate form; and (iii) is present in the dosage form in a therapeutically effective amount and such that the ratio of the drug to the one or more absorption enhancers is 1:100,000 to 10:1; and
(C) one or more excipients selected from the group consisting of rate-controlling polymeric materials, diluents, lubricants, disintegrants, plasticizers, anti-tack agents, opacifying agents, pigments, and flavorings.

2. The solid oral dosage form of claim 1, wherein the pharmaceutical composition has thereon an enteric coating.

3. The solid oral dosage form of claim 2, wherein the enteric-coated composition is a tablet.

4. The solid oral dosage form of claim 1, including a capsule which contains said pharmaceutical composition and which has thereon an enteric coating.

5. The solid oral dosage form of claim 1, wherein the absorption enhancer is selected from the group consisting of sodium caprylate, sodium caprate and sodium laurate.

6. The solid oral dosage form of claim 5, wherein the absorption enhancer is sodium caprate.

7. The solid oral dosage form of claim 1, wherein the bisphosphonate is alendronate.

8. The solid oral dosage form of claim 1, wherein the bisphosphonate is etidronate.

9. The solid oral dosage form of claim 7, wherein the absorption enhancer is sodium caprate and the ratio of the alendronate to the sodium caprate is 1:1000 to 10:1.

10. The solid oral dosage form of claim 3, wherein the absorption enhancer is sodium caprate.

11. The solid oral dosage form of claim 3, wherein the tablet is a sustained-release tablet.

12. The solid oral dosage form of claim 11, wherein one of the excipients is a rate-controlling polymeric material.

13. The solid oral dosage form of claim 12, wherein the rate-controlling polymeric material is hydroxypropyl-methylcellulose.

14. The solid oral dosage form of claim 3, wherein the tablet is an instant-release tablet.

15. The solid oral dosage form of claim 3, wherein the enteric coating comprises a polymer selected from the group consisting of poly(acrylic acid), polyacrylate, poly(methacrylic acid), polymethacrylate, and mixtures thereof.

16. The solid oral dosage form of claim 1, wherein the pharmaceutical composition is in the form of a multiparticulate.

17. The solid oral dosage form of claim 16, wherein the multiparticulate is in the form of a tablet.

18. The solid oral dosage form of claim 1, wherein the pharmaceutical composition includes at least two absorption enhancers.

19. The solid oral dosage form of claim 1, wherein one of the excipients is a rate-controlling polymeric material.

20. The composition of claim 1, wherein one of the excipients is a diluent which is an inert filler selected from the group consisting of microcrystalline cellulose, lactose, dibasic calcium phosphate, saccharides and mixtures of any of the foregoing.

21. The composition of claim 20, wherein the inert filler is microcrystalline cellulose.

22. The composition of claim 20, wherein the inert filler is a lactose selected from the group consisting of lactose monohydrate and lactose anhydrous.

23. The composition of claim 20, wherein the inert filler is a saccharide selected from the group consisting of mannitol, starch, sorbitol, sucrose, and glucose.

24. The composition of claim 23, wherein the saccharide is sorbitol.

25. The composition of claim 1, wherein one of the excipients is a lubricant selected from the group consisting of colloidal silicon dioxide, talc, magnesium stearate, calcium stearate, and stearic acid.

26. The composition of claim 25, wherein the lubricant is stearic acid.

27. The composition of claim 1, wherein one of the excipients is a disintegrant selected from the group consisting of lightly crosslinked polyvinylpyrrolidone, corn starch, potato starch, maize starch and modified starches, croscarmellose sodium, crospovidone, and sodium starch glycolate.

28. The composition of claim 27, wherein the disintegrant is crospovidone.

29. The composition of claim 27, wherein the disintegrant is polyvinylpyrrolidone.

30. A compressible composition which is capable of being compressed into a solid oral pharmaceutical dosage form which is effective in delivering therapeutically effective amounts of a drug and an enhancer, as defined below, to an intestine, said composition consisting of:
(A) a therapeutically effective amount of a bisphosphonate drug in the form of crystalline and/or amorphous particles;
(B) one or more absorption enhancers, each of which: (i) is a solid at room temperature; (ii) is a salt of a medium chain fatty acid having a carbon length of from 8 to 14 carbon atoms in particulate form; and (iii) is present in a therapeutically effective amount and such that the ratio of the drug to the one or more absorption enhancers is 1:100,000 to 10:1; and
(C) one or more excipients selected from the group consisting of rate-controlling polymeric materials, diluents, lubricants, disintegrants, plasticizers, anti-tack agents, opacifying agents, pigments, and flavorings.

31. The composition of claim 30, in the form of a compressible powder or compressible granules.

32. The composition of claim 30, wherein one of the excipients is a rate-controlling polymeric material.

33. The composition of claim 31, wherein one of the excipients is a rate-controlling polymeric material.

34. The composition of claim 30, wherein one of the excipients is a diluent which is an inert filler selected from the group consisting of microcrystalline cellulose, lactose, dibasic calcium phosphate, saccharides and mixtures of any of the foregoing.

35. The composition of claim 34, wherein the inert filler is microcrystalline cellulose.

36. The composition of claim 34, wherein the inert filler is a lactose selected from the group consisting of lactose monohydrate and lactose anhydrous.

37. The composition of claim 34, wherein the inert filler is a saccharide selected from the group consisting of mannitol, starch, sorbitol, sucrose, and glucose.

38. The composition of claim 37, wherein the saccharide is sorbitol.

39. The composition of claim 30, wherein one of the excipients is a lubricant selected from the group consisting of colloidal silicon dioxide, talc, magnesium stearate, calcium stearate, and stearic acid.

40. The composition of claim 39, wherein the lubricant is stearic acid.

41. The composition of claim 30, wherein one of the excipients is a disintegrant selected from the group consisting of lightly crosslinked polyvinylpyrrolidone, corn starch, potato starch, maize starch and modified starches, croscarmellose sodium, crospovidone, and sodium starch glycolate.

42. The composition of claim 41, wherein the disintegrant is crospovidone.

43. The composition of claim 41, wherein the disintegrant is polyvinylpyrrolidone.

44. The composition of claim 30, wherein the absorption enhancer is selected from the group consisting of sodium caprylate, sodium caprate and sodium laurate.

45. The composition of claim 30, wherein the absorption enhancer is sodium caprate.

46. The composition of claim 30, wherein the bisphosphonate is alendronate.

47. The composition of claim 30, wherein the bisphosphonate is etidronate.

48. The composition of claim 46, wherein the absorption enhancer is sodium caprate and the ratio of the alendronate to the sodium caprate is 1:1000 to 10:1.

49. The composition of claim 30, wherein the composition includes at least two absorption enhancers.

50. A solid oral dosage form which is effective in delivering a drug and an enhancer, each as defined below, to an intestine and which comprises an enterically coated pharmaceutical composition consisting of:
(A) a therapeutically effective amount of a bisphosphonate drug in the form of crystalline and/or amorphous particles;
(B) sodium caprate, which: (i) is in particulate form; and (ii) is present in the dosage form in a therapeutically effective amount and such that the ratio of the drug to the one or more absorption enhancers is 1:1,000 to 10:1; and
(C) one or more excipients selected from the group consisting of rate-controlling polymeric materials, diluents, lubricants, disintegrants, plasticizers, anti-tack agents, opacifying agents, pigments, and flavorings.

51. The solid oral dosage form of claim 50, wherein the bisphosphonate is alendronate.

52. A compressible composition which is capable of being compressed into a solid oral pharmaceutical dosage form which is effective in delivering therapeutically effective amounts of a drug and an enhancer, as defined below, to an intestine, said composition consisting of:
(A) a therapeutically effective amount of a bisphosphonate drug in the form of crystalline and/or amorphous particles;
(B) sodium caprate, which: (i) is in particulate form; and (ii) is present in a therapeutically effective amount and such that the ratio of the drug to the one or more absorption enhancers is 1:1,000 to 10:1; and
(C) one or more excipients selected from the group consisting of rate-controlling polymeric materials, diluents, lubricants, disintegrants, plasticizers, anti-tack agents, opacifying agents, pigments, and flavorings.

53. The composition of claim 52, wherein the bisphosphonate is alendronate.

* * * * *

UNITED STATES PATENT AND TRADEMARK OFFICE
CERTIFICATE OF CORRECTION

PATENT NO.       : 7,658,938 B2                                    Page 1 of 1
APPLICATION NO.  : 09/510560
DATED            : February 9, 2010
INVENTOR(S)      : Cumming et al.

It is certified that error appears in the above-identified patent and that said Letters Patent is hereby corrected as shown below:

On Title Page:
Item 73, Assignee: Please correct "Merrion Reasearch III Limited"
                   to read -- Merrion Research III Limited --

Signed and Sealed this

Seventeenth Day of August, 2010

David J. Kappos
*Director of the United States Patent and Trademark Office*